(12) United States Patent
Menon et al.

(10) Patent No.: US 10,893,931 B2
(45) Date of Patent: Jan. 19, 2021

(54) STRONG, FLEXIBLE, AND THROMBUS-FREE WOVEN NANOTEXTILE BASED VASCULAR GRAFTS, AND METHOD OF PRODUCTION THEREOF

(71) Applicant: Amrita Vishwa Vidyapeetham, Kochi (IN)

(72) Inventors: Deepthy Menon, Kochi (IN); John Joseph, Kochi (IN); Praveen Varma, Kochi (IN); Shantikumar Nair, Kochi (IN)

(73) Assignee: Amrita Vishwa Vidyapeetham, Kochi (IN)

( * ) Notice: Subject to any disclaimer, the term of this patent is extended or adjusted under 35 U.S.C. 154(b) by 114 days.

(21) Appl. No.: 16/161,297

(22) Filed: Oct. 16, 2018

(65) Prior Publication Data

US 2019/0110883 A1 Apr. 18, 2019

(30) Foreign Application Priority Data

Oct. 16, 2017 (IN) .............................. 201741036716

(51) Int. Cl.
*D03D 37/00* (2006.01)
*A61F 2/07* (2013.01)
(Continued)

(52) U.S. Cl.
CPC .................. *A61F 2/07* (2013.01); *A61F 2/06* (2013.01); *D03D 3/02* (2013.01); *D03D 15/0027* (2013.01);
(Continued)

(58) Field of Classification Search
CPC .... D04C 1/06; D04C 3/48; D04C 1/02; A61F 2220/0033; A61F 2/07; A61F 2/88;
(Continued)

(56) References Cited

U.S. PATENT DOCUMENTS 3,584,658 A * 6/1971 Ferreirinha ............ D03D 37/00
139/16
3,781,954 A * 1/1974 Stewart ..................... D04B 3/00
28/150

(Continued)

FOREIGN PATENT DOCUMENTS

WO 2013154612 A2 10/2013
WO 2014100718 A1 6/2014

*Primary Examiner* — Robert H Muromoto, Jr.
(74) *Attorney, Agent, or Firm* — Convergence Intellectual Property Law P.C.; Jonathan Garfinkel

(57) ABSTRACT

An apparatus for fabrication of a woven tubular nanotextile used in vascular graft applications. The woven nanotextile conduit is 0.1 to 50 mm in diameter and includes a multitude of hierarchically arranged nanofibers. They are made from low strength bundled nanoyarns containing thousands of nanofibers with improved mechanical strength. The weaving apparatus interweaves the warp and weft yarns in longitudinal and transverse directions, resulting in a flexible and strong woven product. The physical and biological properties of the woven nanotextile were significantly enhanced when compared to non-woven nanofibrous form and conventional medical textiles. The nanotextile displayed superhydrophilic behavior in an otherwise hydrophobic material and when implanted as a vascular graft was robust, suturable, kink-proof and non-thrombogenic, with complete endothelialization of the graft luminal area.

1 Claim, 18 Drawing Sheets

(51) Int. Cl.
  *D03D 15/00* (2006.01)
  *D03D 3/02* (2006.01)
  *A61F 2/06* (2013.01)
  *D03D 25/00* (2006.01)

(52) U.S. Cl.
  CPC . *D03D 2700/0174* (2013.01); *D03D 2700/03* (2013.01); *D10B 2331/00* (2013.01); *D10B 2509/06* (2013.01)

(58) Field of Classification Search
  CPC .... A61F 2/90; D01D 5/0076; D10B 403/033; D03D 3/02; D03D 23/00; D03D 25/00; D03D 25/005; D03D 37/00; D03D 41/00; D03D 41/004
  See application file for complete search history.

(56) References Cited

U.S. PATENT DOCUMENTS

| | | | |
|---|---|---|---|
| 3,791,418 A * | 2/1974 | Pfarrwaller | D03D 47/00 139/453 |
| 3,903,930 A * | 9/1975 | Muller | D03D 35/00 139/453 |
| 4,050,481 A * | 9/1977 | Muller | D03D 47/266 139/436 |
| 4,577,665 A * | 3/1986 | Diesner | D03D 47/04 139/104 |
| 5,508,775 A * | 4/1996 | Mizuno | D06C 7/00 26/106 |
| 5,653,267 A * | 8/1997 | Graser | D03J 1/001 139/1 R |
| 6,409,750 B1 * | 6/2002 | Hyodoh | A61F 2/07 623/1.1 |
| 7,135,040 B2 * | 11/2006 | Wang | D04C 1/02 623/1.51 |
| 7,275,471 B2 * | 10/2007 | Nishri | D04C 1/02 87/13 |
| 7,413,575 B2 | 8/2008 | Phaneuf et al. | |
| 7,550,006 B2 | 6/2009 | Nunez et al. | |
| 7,922,761 B2 | 4/2011 | Shalev et al. | |
| 8,192,481 B2 | 6/2012 | King et al. | |
| 9,402,753 B2 | 8/2016 | Du et al. | |
| 9,970,137 B2 * | 5/2018 | Lorenzo | A61F 2/90 |
| 2002/0111674 A1 * | 8/2002 | Chouinard | A61F 2/90 623/1.35 |
| 2004/0073300 A1 * | 4/2004 | Chouinard | D04C 3/48 623/1.53 |
| 2004/0098099 A1 * | 5/2004 | McCullagh | D04C 1/06 623/1.15 |
| 2005/0257674 A1 * | 11/2005 | Nishri | D04C 3/18 87/11 |
| 2006/0070516 A1 * | 4/2006 | McCullagh | A61F 2/90 87/9 |
| 2009/0005847 A1 * | 1/2009 | Adams | D04C 3/48 623/1.2 |
| 2009/0188380 A1 * | 7/2009 | Dow | H04N 21/812 87/11 |
| 2011/0203446 A1 * | 8/2011 | Dow | D04C 1/06 87/11 |
| 2012/0186420 A1 * | 7/2012 | Lilburn | D04C 3/48 87/33 |
| 2012/0330398 A1 * | 12/2012 | Hyodoh | A61F 2/01 623/1.11 |
| 2013/0060323 A1 * | 3/2013 | McHugo | A61F 2/90 623/1.18 |
| 2013/0167710 A1 * | 7/2013 | Dow | D04C 3/30 87/9 |
| 2014/0035183 A1 * | 2/2014 | Scherrible | A61F 2/06 264/103 |
| 2016/0168754 A1 * | 6/2016 | Menon | D02G 3/36 264/465 |
| 2019/0262151 A1 * | 8/2019 | Treacy | A61F 2/90 |
| 2019/0352813 A1 * | 11/2019 | Tolle | D03D 47/125 |

* cited by examiner

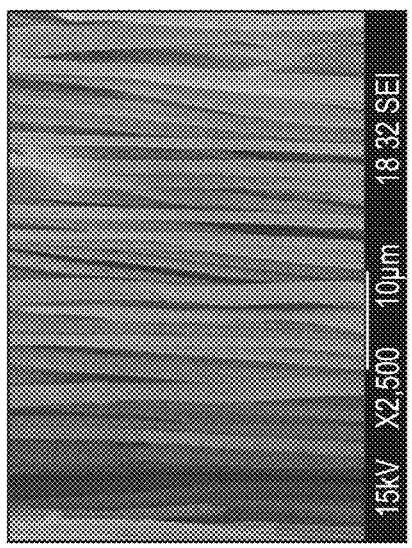
FIG. 6B
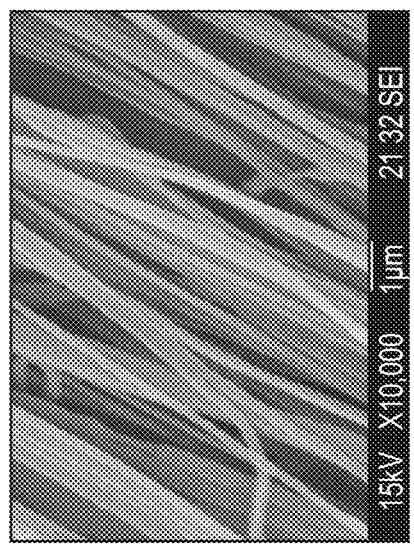
FIG. 6C
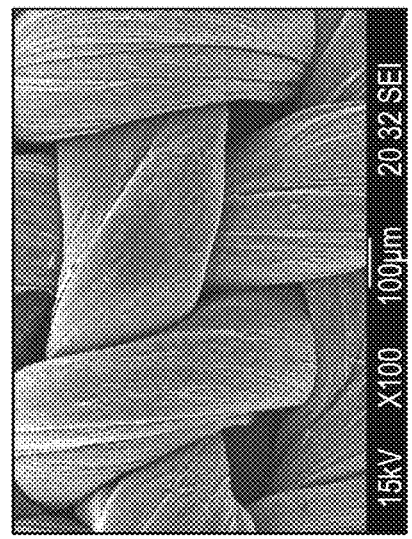
FIG. 6E
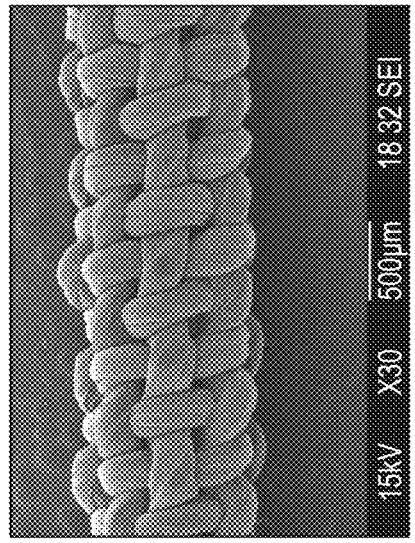
FIG. 6F
FIG. 6A
FIG. 6D
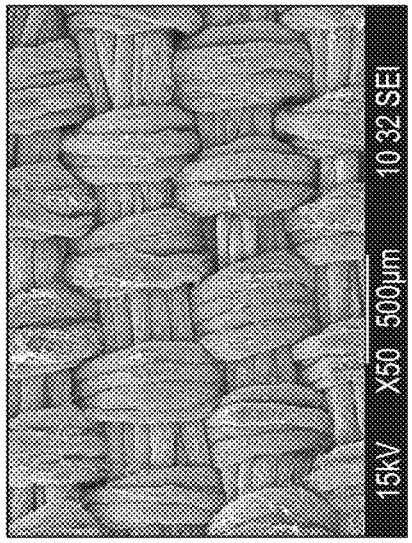

STRONG, FLEXIBLE, AND THROMBUS-FREE WOVEN NANOTEXTILE BASED VASCULAR GRAFTS, AND METHOD OF PRODUCTION THEREOF

CROSS-REFERENCES TO RELATED APPLICATIONS

This application claims priority to Indian Provisional Patent Application No. 201741036716 entitled "VASCULAR GRAFTS, METHODS OF PRODUCTION THEREOF AND MACHINES FOR PRODUCTION THEREOF" filed on Oct. 16, 2017, the full disclosure of which is incorporated herein by reference.

FIELD OF THE INVENTION

The present invention generally relates to tubular conduits and in particular to vascular graft devices developed from polymeric nanofibrous yarns by the process of weaving and its methods of preparation thereof.

BACKGROUND

Autologous vein grafts remain the gold standard material in bypass surgery of small and medium sized blood vessels. The limited availability of autologous graft conduits and the widespread prevalence of vein graft diseases has led to search for synthetic graft substitutes. A few of such biologically compatible substrate materials include the widely used thermoplastics such as polyesters, PTFE, silicone and polyurethanes.

Synthetic substitutes based on polyethylene terephthalate (PET, Dacron) and expanded polytetrafluoroethylene (ePTFE) have been suggested for limited therapeutic applications. Polyester based fibers like Dacron are available in knitted or woven forms from monofilament or multifilament conventional yarns. Polyester-based fibers being in the micron range have been manipulated into different forms such as woven or knitted, with or without a velour construction. Synthetic vascular conduits which take the form of warp-knit, warp knit double-velour, woven double-velour graft, woven graft with single velour and woven grafts containing annular rings have been attempted. Extruded tubes of PTFE as medium and large diameter conduits have been described to have good biocompatibility and low thrombogenicity. Some PTFE based small diameter (<6 mm) conduit has also been described. A few of the marketed small diameter peripheral grafts based on PTFE are from Gore-Tex™ (Internal diameter: 3-5 mm), Exxcel Soft Grafts from Atrium of Internal diameter 4-6 mm, Impra™ grafts based on ePTFE from Bard Peripheral Vascular™(ID: 3-5 mm) and Taperflo™ gelatin coated ePTFE graft from Vascutek Terumo™ (ID: 4-6 mm). However, such conduits have been restricted to certain biomedical applications due to its non-biodegradability, compatibility, and low patency.

Electrospun fibers have been used to develop conduits for applications such as nerve guides and vascular conduits. Currently, 3-D synthetic tubular conduits are constructed by either suturing a 2D polymeric sheet into a tubular form or by electro spinning polymeric solution onto a rotating mandrel. This would help to generate different topographies in the luminal side of the conduits which can render varied mechanical and biological responses. Small diameter vascular grafts based on biodegradable polymers have been processed by the technique of electrospinning.

The document U.S. Pat. No. 6,409,750B1 describes a bifurcated and trifurcated woven stent, which is made of Dacron, polyurethane or PTFE by hand or machine weaving. The diameters of the stents mentioned range from 5.5 mm up to 40 mm. However, issues related to biodegradability, compatibility, limitations in use and patency exists in such stents. U.S. Pat. No. 9,402,753 B2 describes a large diameter woven prosthesis manufactured by a weaving technology using PET fibers, elaborating on the method of making the same to varied diameters and lengths. The document U.S. Pat. No. 7,135,040B2 details an apparatus with a cylindrical mandrel for manufacturing micro braided tubular nerve guide conduit made from poly (L-lactide-co-glycolide) fiber and chitosan. The fibers used have a diameter of about 20 microns. The document U.S. Pat. No. 7,550,006 B2 elucidates a flat woven implantable tubular prosthesis having an inner diameter of one of its lumen to be between 10-12 mm. The document U.S. Pat. No. 8,192,481B2 discloses a vascular graft made of a layer of ePTFE along with a biodegradable layer and a fabric layer. The ePTFE layer of the graft is cross linked with the biodegradable layer. The additional biodegradable layer added to make the graft compatible has a negative effect on the patency of the graft. The PCT publication WO2013154612A2 describes core-sheath grafts developed using poly (glycerol sebacate) (PGS) and electrospun poly (caprolactone) (PCL) sheath, coated with a thromboresistant agent, viz., heparin. The graft was cut into small cross sections of 4 mm in this case, and adding heparin provided prolonged patency in the vascular graft. The PCT publication WO2014100718A1 describes a method of preparing fibrous constructs by electrospinning PGS in combination with a heat resistant carrier polymer (PVA, PHB, PET, PDO, or PLA and their combinations) to form tubular conduits of <4 mm which is further crosslinked by heat curing. The document U.S. Pat. No. 7,413,575B2 describes a textile conduit made from nanofibrous biocomposite material consisting of a synthetic polymer and an extracellular matrix protein, fabricated to diameters in the range of <6 mm by an electrospinning perfusion process. The document U.S. Pat. No. 7,922,761B2 describes a multilayered tubular conduit of <6 mm by electrospinning polymers of polyurethane derivatives with different thrombogenic agents. The small diameter vascular graft is produced by a hybrid method, wherein the luminal surface was comprised of a micropattern of grooves to facilitate cell adhesion and the exterior surface was made of electrospun microfibers that provided mechanical properties to the graft. A modified electrospinning apparatus is described in US patent publication, US20160168754A1 for fabrication of nanoyarns.

Although these documents describe grafts made from electrospinning, none of these electrospun products are made by weaving of nanofibrous yarns. Electrospun non-woven fibers give poor mechanical properties and have not been found suitable for vascular conduit applications. Another shortcoming in these disclosures is the lack of machines for automated production of electrospun woven conduits which greatly improves the capability to modify the structure and functional properties of these yarns and improve their efficiency. There is need for an apparatus which overcomes the shortcoming of existing art in the domain.

Diverse approaches to develop alternative materials and techniques are essential to fabricate synthetic graft substitutes that possess adequate mechanical properties (e.g., resilience, burst strength, flexibility, kink resistance) with good bio/hemocompatibility, endothelialization, non-thrombogenecity and patency. Specifically, small diameter (<6 mm) conduits with improved functionality and patency are needed. Present day small diameter vascular grafts fail in terms of their patency. None of these conduits have shown acceptable patency at smaller diameters.

SUMMARY OF THE INVENTION

The invention in its various aspects relates to woven nanotextile conduits, a weaving apparatus for making nanotextile conduits, a method of fabricating nanotextile conduits using the weaving apparatus, and a method of using the nanotextile conduits as vascular grafts or in tissue engineering applications. The medical nanotextile combines the nanoscale properties of individual nanofibers and the robust mechanical strength of bundled nanofibrous yarns. The implanted nanotextile vascular graft showed comparable mechanical properties, with higher patency as against the commercial standard ePTFE.

In one aspect, a vascular graft from tubular woven nanotextile conduit in the diameter range of 0.1 to 50 mm is included. The conduit includes a plurality of warp yarns interwoven with a weft yarn to form a hierarchical structure. Each of the plurality of the warp yarns comprises a first set of polymeric yarn fibers with a diameter in the range of 1 to 1000 µm. The weft yarn comprises a second set of polymeric yarn fibers (323) with a diameter in the range of 1 to 5000 µm. In some aspects, the first and second set of polymeric yarn fibers comprises a polymer selected from the group of polyesters, polyether, polyanhydrides, polycarbonates, polyphosphazenes, poly(amino acids), polypeptides, glycosaminoglycan, polysaccharides, polydioxanone (PDO), poly(lactide-coglycolide) (PLGA), polyglycolic acid (PGA), polylactic acid (PLA), and polycaprolactone (PCL). In some aspects, the first and second set of polymeric yarn fibers further comprises biomolecules selected from the group of collagen, elastin, gelatin, fibrin, fibronectin, chitin, chitosan and laminin. In one aspect, the individual fiber diameter of the yarn fibers is in the range of 10 to 5000 nm. In another aspect, the packing density of the conduit is in the range of 50 to 1000 interweaves per $cm^2$. In yet another aspect, sidewall thickness of the graft is in the range of 100 to 750 µm. In some aspects, the first set and second set of polymeric yarn fibers are bundled polymeric yarn fibers. In some other aspects, the first set and second set of polymeric fibers are electrospun polymeric yarn fibers.

In one aspect, a weaving apparatus comprising a drum assembly mounted on a supporting platform is included. The drum assembly comprises a first set of shuttling rods attached equidistant along the circumference of a first disc and a second set of shutting rods attached equidistant along the circumference of a second disc. The first set and second set of shuttling rods are aligned to form a closed drum assembly. The drum assembly includes a stationary carrier comprising a bobbin loaded with nano- or micro-fiber based polymeric weft yarn. The drum assembly includes a plurality of movable carriers loaded in each of the first set of shuttling rods. Each of the movable carriers comprise bobbins loaded with nano- or micro-fiber based polymeric warp yarns. The movable carriers are configured to shuttle between the first set of rods and the second set of rods on alignment thereby interlocking the nano- or micro-fiber based warp and weft yarn. The drum assembly includes a weaving rod of predetermined diameter mounted on the first disc. The rod is configured to secure the warp yarns and the base weft yarns from the carriers at predetermined tension. The supporting platform includes a geared motor system configured for synchronous rotation of the first and second discs after shuttling of each movable carrier to form a woven conduit.

In one aspect, a method of preparing a tubular woven nanotextile conduit using the weaving apparatus is included. The method includes loading the plurality of movable carriers comprising bobbins loaded with nano or micro-fiber based warp yarn and the stationary carrier comprising bobbin loaded with base weft yarn, securing the warp yarns and weft yarn to the weaving rod at predetermined tension to form a starting point of the woven conduit, aligning the first set of shuttling rods with the second set of shuttling rods, shuttling one or more warp carriers across aligned shuttling rods to interlock with the base weft yarn, rotating the first and second discs synchronously, and repeating the shuttling and rotating steps to form a woven conduit. In some aspects, the curvature of the conduit is adjusted by changing the radius of curvature of the weaving rod. In other aspects, the packing density of the conduit is controlled by varying the number of carriers or by changing the diameter of warp/weft yarns used in the weaving process. In yet other aspects, the method includes drawing the woven conduit continuously through an orifice in the apparatus.

This and other aspects are disclosed herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 6A, 6B, and 6C illustrate SEM micrographs of a PCL-collagen woven conduit.

FIGS. 6D, 6E and 6F, illustrate SEM micrographs of a PLLA woven conduit.

Referring to the drawings, like numbers indicate like parts throughout the views.

DETAILED DESCRIPTION

Figure 1A:
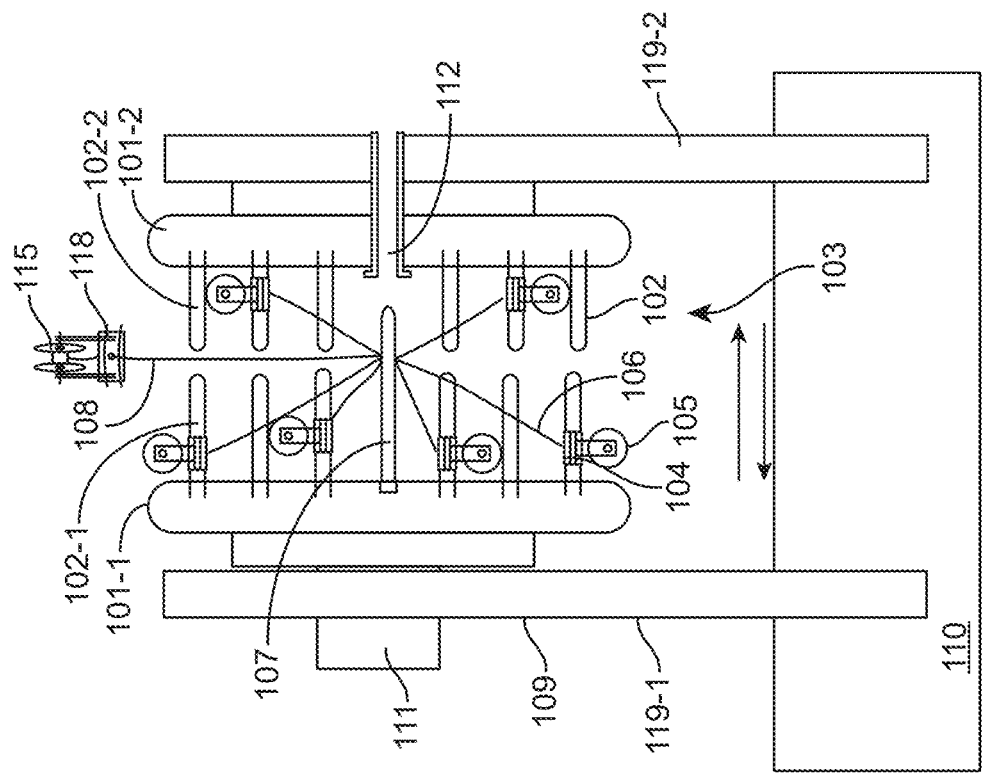
FIG. 1A shows open configuration of the weaving apparatus.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration". Any implementation described herein as "exemplary" is not necessarily to be construed as advantageous over other implementations.

As used herein, the term "yarn" refers to polymeric fibers which may include bundled nanofibers in the range of 150-1500 nm.

As used herein, the term "woven nanotextile" refers to construct that has been made by interweaving of multiple nanofibrous yarns As used herein, the term "tubular" refers to any tube-like structure having walls defining a lumen and having a constant or variable diameter throughout its length.

As used herein, the term "graft" or "conduit" refers to any tubular structure which is suitable for use in biomedical applications such vascular prosthesis, vascular occlusion, or as a scaffold for tissue engineering, for example, as a vascular access graft, a vascular shunt such as an arteriovenous shunt, a replacement for blood vessel, a bypass vascular prosthesis and the like.

The terms LI, MI, and HI are used to refer to the interweaves per unit area, with LI corresponding to ~63 interweaves/cm$^2$, MI ~100 interweaves/cm$^2$ and HI 330 interweaves/cm$^2$.

As used herein the term "about" refers to ±20%, ±10%, ±5%, ±1%, or less, or any number therebetween.

The present invention in its various embodiments discloses a cylindrical weaving machine/apparatus/system for fabrication of tubular conduits, a method for automated fabrication of a tubular conduit, a fabricated nanotextile conduit for vascular prosthesis or as a scaffold for tissue engineering, and a method of use of the conduit in medical applications such as vascular bypass or tissue engineering.

Figure 1B:
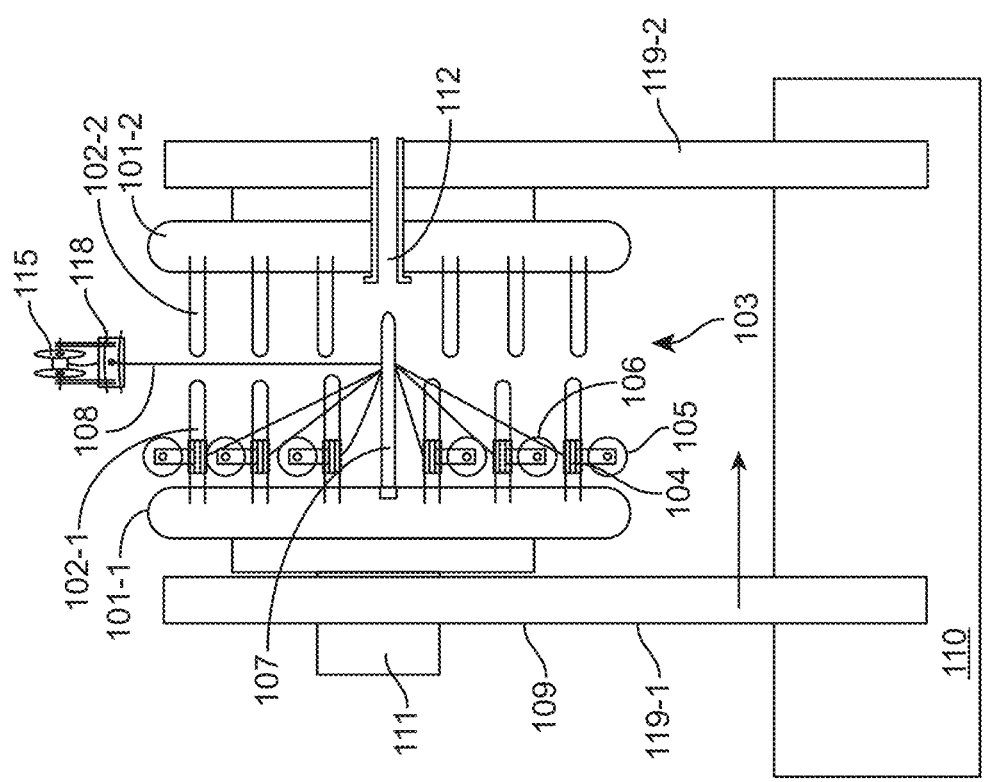
FIG. 1B shows the closed configuration of the weaving apparatus.

Referring now to FIGS. 1A and 1B, an apparatus 100 for weaving tubular nanotextile conduits is illustrated according to one embodiment of the invention. The apparatus 100 is a low tension weaving apparatus. The weaving apparatus 100 includes a drum assembly 103 mounted on a supporting platform 109. The drum assembly 103 may include identical sized discs 101-1 and 101-2 configured to coaxially rotate about the supporting platform. The discs 101-1,101-2 include an inner surface for mounting a set of shuttling rods 102-1, 102-2 and an outer surface in contact with the supporting platform 109. In some embodiments, a plurality of movable carriers 104 are loaded in the first set of shuttling rods 102-1 in an open drum configuration, as shown in FIG. 1A. Each of the movable carriers 104 may contain bobbins 105 that are loaded with electrospun yarns which constitute longitudinal yarns or warp yarns 106 of the tubular conduit. A stationary carrier 118 may be loaded with a bobbin 115 for providing electrospun yarns which constitute a single circumferential yarn or weft yarn 108 of the tubular conduit. In some embodiments, a weaving rod 107 of predetermined diameter secures the warp yarns 106 and weft yarn 108 centrally in the drum assembly 103 at predetermined tension. The woven conduit formed on the weaving rod 107 is drawn out through an orifice 112.

The discs 101-1, 101-2 are assembled such that the shuttling rods 102-1, 102-2 in each disc align to form a closed drum configuration, as shown in FIG. 1B. The alignment of the discs 101-1, 101-2 in closed drum configuration facilitates smooth movement of carriers 104 between the first set of shuttling rods 102-1 and second set of shuttling rods 102-2. The supporting platform 109 may include a set of clamps 119-1 and 119-2 for holding the drum assembly 103 on a common base 110. A geared motor system 111 may provide one step rotation of the drum assembly 103 after each shuttling of a single warp carrier 104 for synchronous rotation of the two discs of the drum.

Each disc 101 may further include a ring structure 141-1,141-2 for mounting the set of shuttling rods 102. The set of shuttling rods 102 may be mounted perpendicular to each disc 101 to form the drum assembly 103. Each rod of the set of shuttling rods 102 may be mounted at a fixed angle about the axis of the disc 101. Typically, the rods are placed equidistant along the circumference of each of the discs. The electrospun warp yarns 106 are drawn through orifice 112 in the movable carrier. The yarns may be maintained at a constant tension.

Figure 1C:
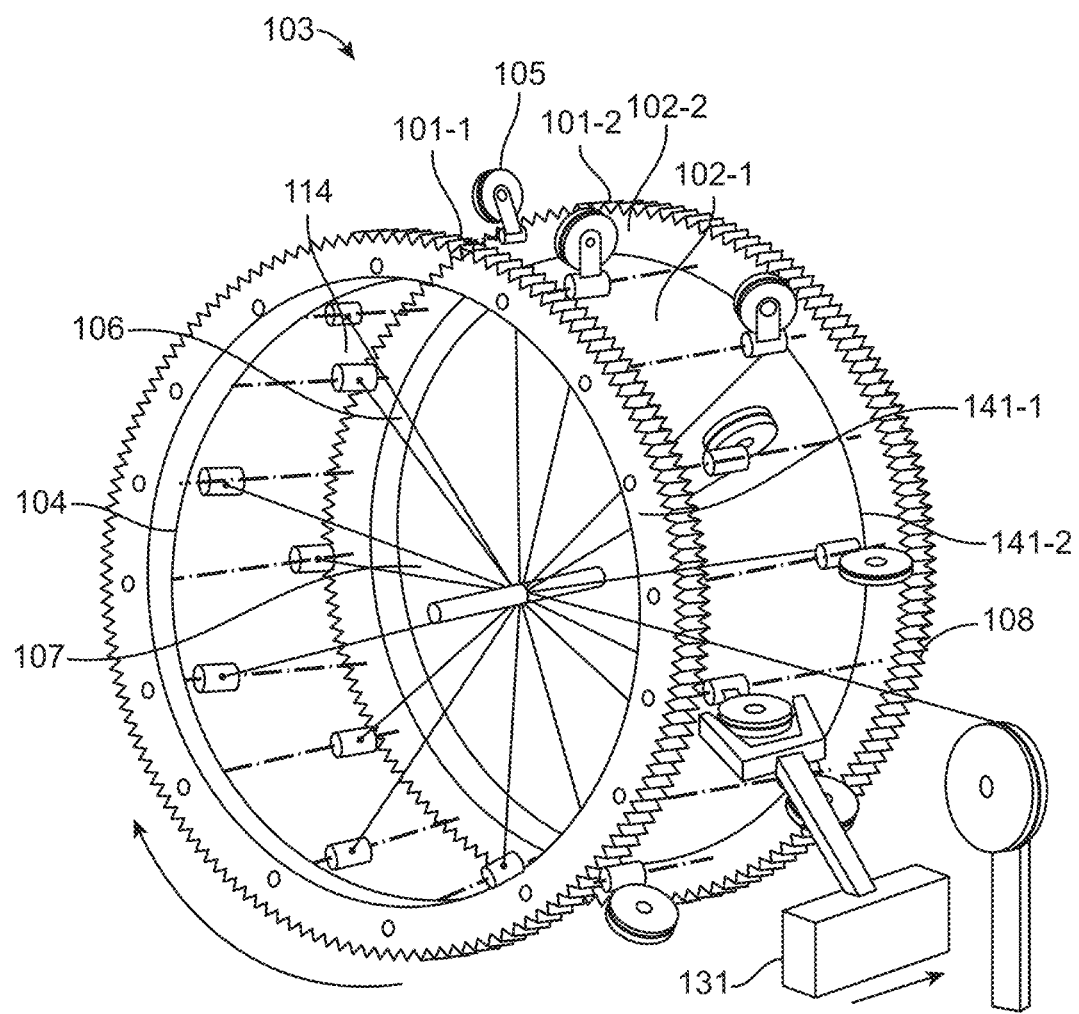
FIG. 1C shows a 3 dimensional perspective of the rotating drum assembly.

Referring now to FIG. 1C, a mounted drum assembly 103 for fabrication of woven tubular conduits is illustrated according to one embodiment of the invention. The production of the nanotextile conduit occurs by interweaving of mutually perpendicular warp yarns and weft yarns in a step-wise manner. This step-by-step interweaving enables low tension weaving, ideal for low strength yarns. In some embodiments, the apparatus also includes a shuttling mechanism 131 to move the carriers 104 across the aligned shuttling rods automatically. In some embodiments, the apparatus is configured to actuate the geared motor system 111 for providing synchronous disc rotation in the drum assembly 103.

In various embodiments, the plurality of shuttling rods 102 on each disc 101 contains at least 2, more typically 7 to 300, individual shuttling rods. In various embodiments, movable carriers 104 maybe loaded on some or all of the shuttling rods.

In various embodiments, the diameter of the conduit is determined by the diameter of the weaving rod. In some embodiments, the weaving rod 107 is detachably mounted from one end of the drum assembly 103. In some embodiments, the weaving rod is curved. In some embodiments, the diameter of the weaving rod is adjustable. In some embodiments, the curvature of the weaving rod is adjustable. In some embodiments, the curved weaving rod is configured such that the longitudinal warp yarns and circumferential weft yarn meet at an angle of less than 90° which imparts flexibility and high kink resistance. In some embodiments, the longitudinal warp yarns and circumferential weft yarn meet at an angle of 70° to 88°. In some embodiments, the weaving rod is mounted via the disc 101-1. In some embodiments, the diameter of weaving rod is in the range of 0.5-50 mm.

The apparatus described herein allows for fabricating tightly packed material with an overall reduction in tension requirements for the nanoyarns which allows for weaving of low strength materials resulting in woven tubular conduits which meet the stringent demands for use in vascular prosthesis or as a scaffold for tissue engineering, such as a vascular graft or conduits for other biomedical applications.

Figure 2:
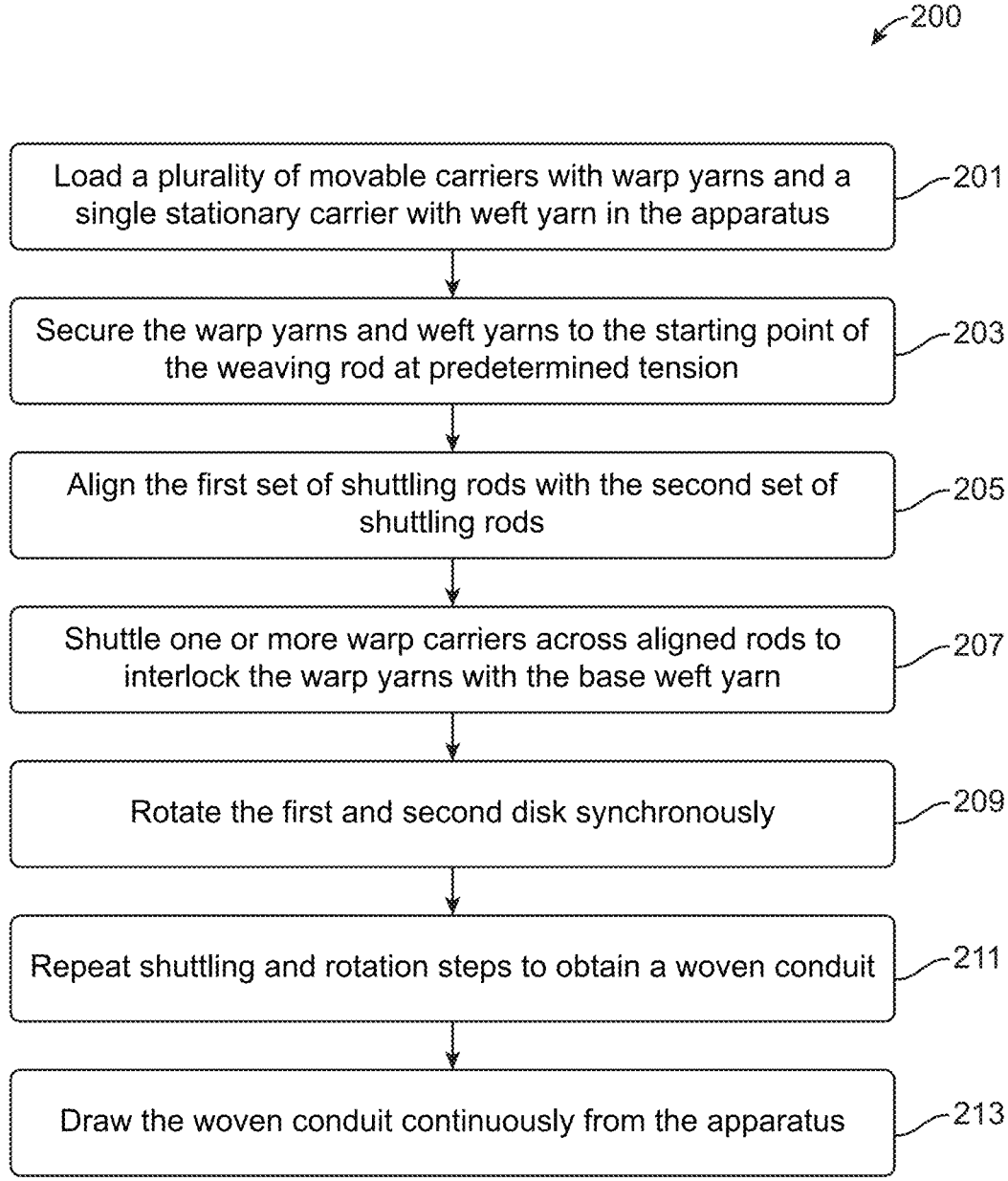
FIG. 2 shows a method of fabricating a conduit using the weaving apparatus.

Referring now to FIG. 2, a method 200 for weaving tubular conduits using the weaving apparatus 100 is illustrated, according to one embodiment of the invention. The method is based on single-step weaving of conduit onto the weaving rod using a single weft that interlocks various warps. The movable carriers containing warp yarns and the stationary carrier containing weft yarn are loaded to the first set of shuttling rods of the apparatus, in block 201. The warp yarns and weft yarn are secured at predetermined tension to the starting point of the weaving rod of the apparatus, in block 203. The first set of shuttling rods is aligned with second set of shuttling rods to form a closed drum configuration, in block 205. One or more movable carriers are shuttled between the aligned rods to interlock the warp yarns with the weft yarn, in block 207. The drum assembly rotates one step to advance the weaving process, in block 209. The shuttling and rotation steps are repeated in block 211 to obtain a woven conduit. The woven conduit was drawn continuously from the apparatus via an orifice in block 213. In some embodiments, the method is for weaving a curved tubular conduit. The method may include the step of changing the radius of curvature of the weaving rod. The weaving rod interlocks warp and weft yarns at an angles less than 90° i.e., typically between 70° to 88°, which imparts flexibility in addition reduce the radius of curvature of the graft. In various embodiments, the tension of the warp and weft yarns is adjusted based on the strength of the yarns. The tension of the weft yarn loaded in the single stationary carrier is adjusted such that it interlocks the warp yarns drawn from each carrier due to the shuttling mechanism of the warp yarns.

In some embodiments, conduits of different diameters are fabricated by changing the diameter of the weaving rod, with corresponding changes in the number/diameter of longitudinal yarns (N) interlaced per circumferential yarn based on Equation 1, $N=\pi D/d$, wherein D is the diameter of the tubular conduit, d is the diameter of the longitudinal yarn.

In various embodiments, a flexible graft 300 suitable for biomedical applications is provided, as shown in FIG. 3A-E. The graft of the present embodiments is preferably characterized by enhanced physical, mechanical and biological properties. In some embodiments, the graft 300 is suitable for vascular prosthesis. In some embodiments, the graft is configured to: a) increase patency, b) prevent occlusion, c)

prevent leakage, d) prevent thrombus formation, e) prevent aneurysm, and/or f) promotes endotheliazation in a subject for at least 12 h, 24 h, 2 days, 4 days, 8 days, 16 days, 1 month or longer following implantation. In one embodiment, the porosity of the graft 300 is less than 1 mL/cm$^2$/min. In one embodiment, the burst strength of the graft 300 is at least 5000, 10000, or 15000 mm Hg. In some embodiments, the average kink radius of the woven graft 300 is <30 mm, and typically in the range of 1 to 25 mm. In some embodiments, the longitudinal tensile strength of the graft is in the range of 10 to 80 N, typically at least 40 N. In some embodiments, the circumferential tensile strength of the graft is in the range of 10 to 20 N, typically at least 15N. In some embodiments, the radial stiffness of the graft is in the range of 2 to 15 N, typically at least 10N. In some embodiments, the suture retention strength is in the range of 5-60 N, typically at least 20N.

Figures 3A, 3B:
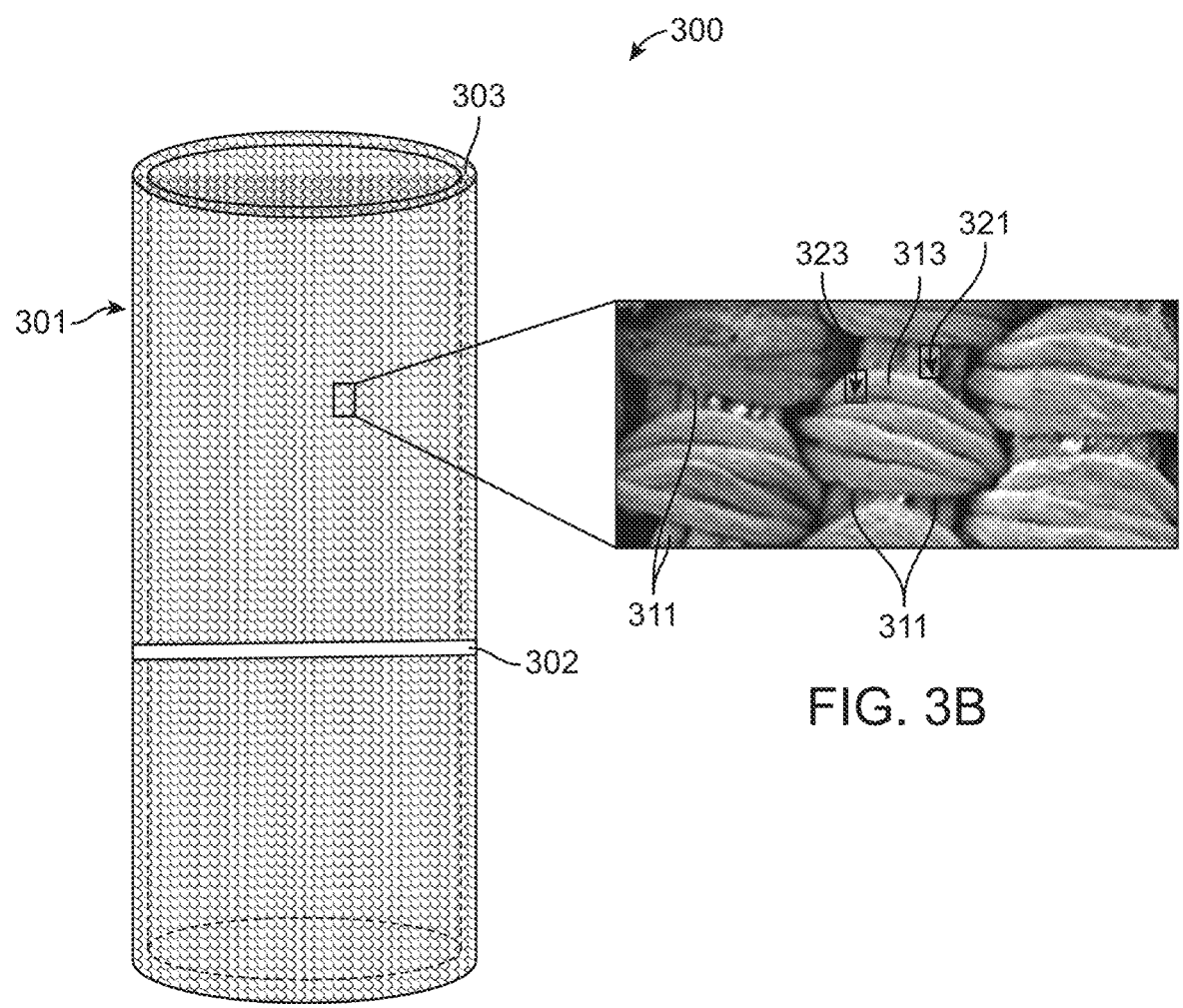
FIG. 3A and 3B illustrates a graft from woven tubular conduit.

Referring now to FIG. 3A, the graft 300 includes at least one woven tubular conduit 301 with a hierarchical nanostructure according to one embodiment of the invention. The tubular conduit 301 may be between 0.1 to 50 mm in diameter 302. The side wall 303 thickness for the tubular conduit is in the range of 1 to 2000 µm, more typically in the range of 100 to 750 µm. The length of the tubular conduit 301 may be in the range of 1 to 500 cm.

Referring now to FIG. 3B, the woven conduit 301 includes a plurality of warp yarns 311 interwoven with a weft yarn 313 according to one embodiment of the invention. The warp yarns 311 include a first set of electrospun polymeric yarn fibers 321. The diameter of the individual yarn in the warp yarn is in the range of 1 to 1000 µm, more typically in the range of 70 to 300 µm. The weft yarn 313 includes a second set of electrospun polymeric yarn fibers 323. The diameter of the individual yarn in the weft yarn is in the range of 1 to 5000 µm, more typically in the range of 70 to 300 µm. The warp yarns 311 and/or weft yarns 313 may be bundled yarns obtained by plying or twisting or bundling of a plurality of electrospun individual nanoyarns. In some embodiments, the warp yarn 311 and/or weft yarn 313 may include 2-20 individual nanoyarns bundled together. The final twist of the yarns may be in the range of 10-150 turns per meter. In some embodiments, the yarns cannot be woven using conventional weaving processes. In some embodiments, the yarns used in weaving have strength of 1:2, 1:4, 1:6, 1:8, 1:10, or lower, of a traditional cotton fiber used in weaving. The warp yarns 311 and/or the weft yarns 313 and may include one or more polymers 312, one or more proteins 322, or a combination thereof, according to one embodiment of the invention. In some embodiments, the warp yarns 311 and/or the weft yarns 313 may include one or more biodegradable polymers. In other embodiments, the warp yarns 311 and/or the weft yarns 313 may include one or more non-biodegradable polymers.

In some embodiments, the warp yarns 311 and/or weft yarns 313 may include one or more polymers selected from the group of polyesters, polyethers, polyanhydrides, polycarbonates, polyphosphazenes, poly (amino acids), polypeptides, glycosaminoglycan, polysaccharides, polydioxanone (PDO), poly (lactide-coglycolide) (PLGA), polyglycolic acid (PGA), polylactic acid (PLA), or polycaprolactone (PCL) and blends or copolymers or proteins or therapeutic agents thereof. In a typical embodiment, the warp yarns 311 and/or weft yarns 313. An electrospun nanoyarn is typically fabricated using an electrospinning apparatus, and more typically using a modified electrospinning apparatus such as those described in US patent publication, US20160168754A1, or the like.

Figure 3E:
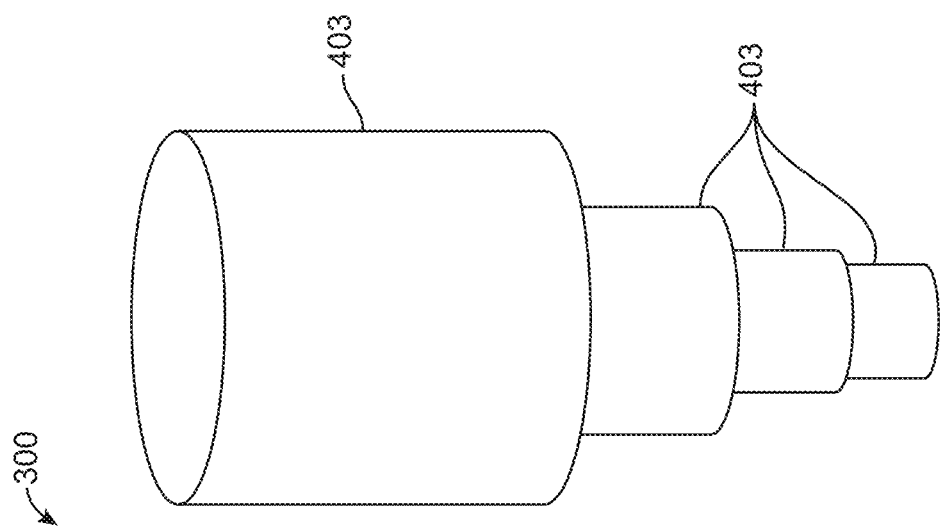
FIG. 3E illustrates a tubular conduit with step changes in diameter.
Figure 3D:
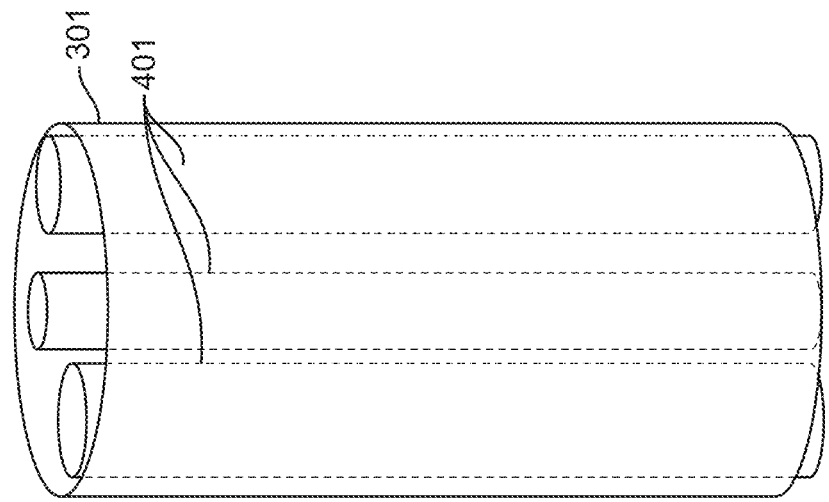
FIG. 3D illustrates a multi-channel tubular conduit.
Figure 3C:
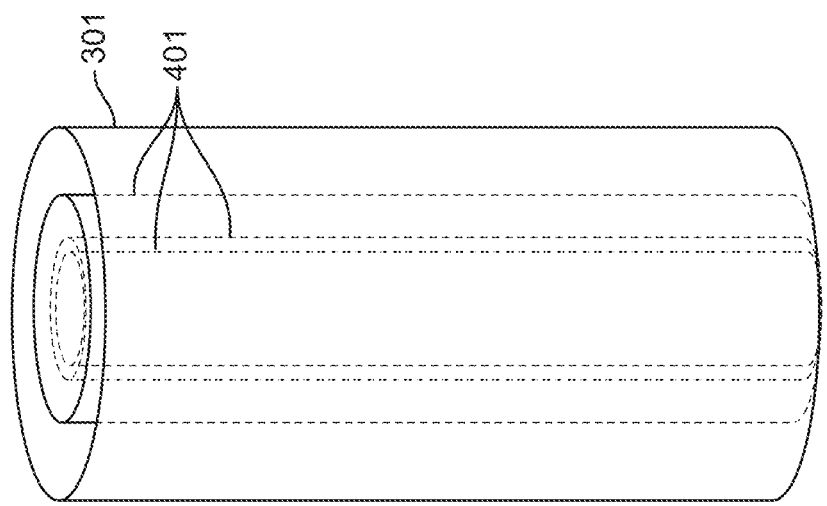
FIG. 3C shows a concentric tubular multi-layer conduit.

In some embodiments, the graft 300 may include at least 1, 2, 3, 4, 5, 6 or more layers of additional tubular conduits 401. Referring now to FIG. 3C, the layers of additional conduits 401 may be oriented as concentric structures according to one embodiment of the invention. Referring now to FIG. 3D, the layers of conduits 401 may be oriented as multi-channeled structures according to another embodiment of the invention. Referring now to FIG. 3E, the conduit may be fabricated as a hierarchical nanostructure with step changes in diameter 403 over the length of the conduit according to yet another embodiment of the invention.

The automated weaving apparatus/system described herein facilitates a single-step weaving method, wherein a weft interlocks a single warp at each step, thus making progress on the weave process step-wise through a precise positioning of the warp within the conduit. This step-by-step weaving approach reduces the force on the weft, in turn reducing the overall tension in each warp and weft, thereby enabling weaving of yarns with high mechanical strength. The method controls the diameter of the woven conduit by varying the diameter of the weaving rod, thereby controlling the compactness, strength and suturable characteristics of the conduit. Furthermore, the weaving method controls the packing density or tightness of the weave by varying the number of longitudinal/warp yarns used in the weaving and thereby varies the graft porosity. The method enables fabrication of a continuous conduit that is seamless and can be made to any desired length, diameter and porosity. The fibers produced by electrospinning, being in the micron to submicron or nano size, closely mimic the native extracellular matrix scaffold within vessels, and mediate cellular interactions and thus may help to emulate the biological properties of blood vessels for vascular applications. The high surface area to volume ratio of electrospun nanofibers increases cellular interactions in comparison to conventional cotton fibers/monofilaments.

A method of treating a disease or disorder by implanting the tubular nanotextile conduits as a vascular graft is disclosed herein according to yet another embodiment of the invention. The method demonstrates superior in vivo efficacy, allows endothelization of cells in the conduits, improved neo-capillary formation, improved short-term and long-term patency, decreased intimal thickening and prevents side effects associated with graft implants such as occlusion, thrombus formation, inflammation response, leakage and aneurysm.

Although the detailed description contains many specifics, these should not be construed as limiting the scope of the invention but merely as illustrating different examples and aspects of the invention. It should be appreciated that the scope of the invention includes other embodiments not discussed herein. Various other modifications, changes and variations which will be apparent to those skilled in the art may be made in the arrangement, operation and details of the system, apparatus and methods of the present invention disclosed herein without departing from the spirit and scope of the invention as described here. While the invention has been disclosed with reference to certain embodiments, examples and claims, it will be understood by those skilled in the art that various changes may be made and equivalents may be substituted without departing from the scope of the invention. In addition, many modifications may be made to adapt to a particular situation or material the teachings of the invention without departing from its scope.

EXAMPLES

Example 1: Fabrication of Small Diameter Conduits (0.5 & 4 mm) of PLLA

Figure 4A:
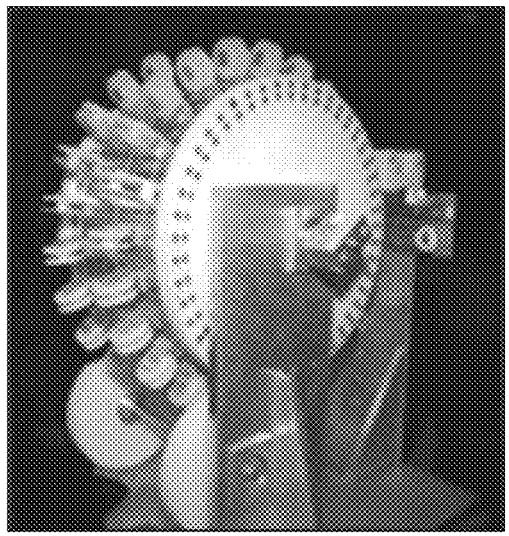
FIG. 4A illustrates an apparatus developed for weaving conduits.
Figure 4B:
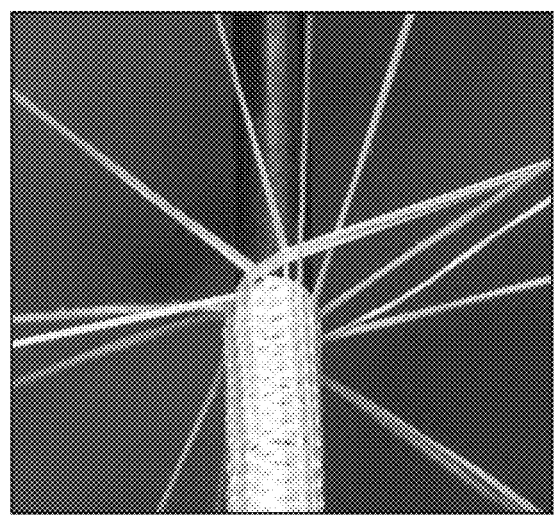
FIG. 4B shows a conduit obtained by single-step weaving onto the weaving rod showing the single weft that interlocks various warps.
Figure 4C:
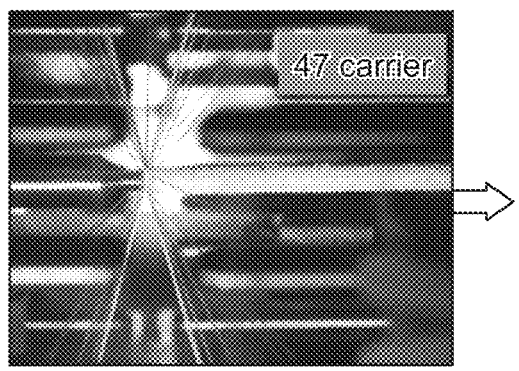
FIG. 4C shows optical image of woven conduit of high packing density with 47 carriers.
Figure 4D:
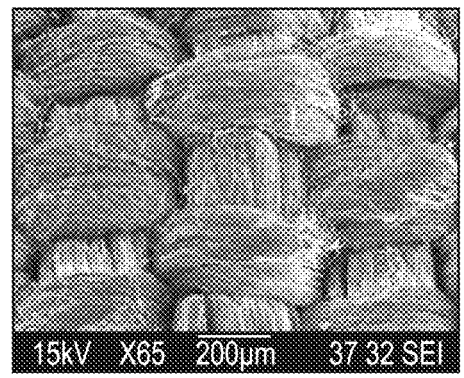
FIG. 4D shows SEM image of woven conduit of high packing (HI) density with 47 carriers.
Figure 4E:
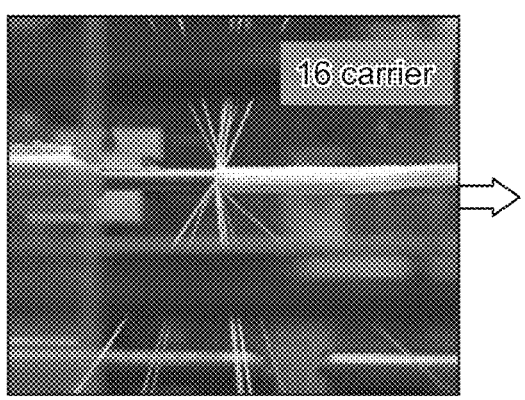
FIG. 4E shows optical image of woven conduit of low packing (LI) density with 16 carriers.
Figure 4F:
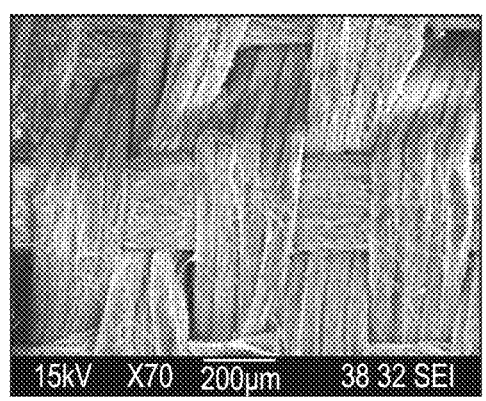
FIG. 4F shows SEM image of woven conduit of low packing density with 16 carriers.

A custom designed weaving apparatus was developed according to the embodiments of the invention, as shown in FIG. 4A. Small diameter conduits (<6 mm) were obtained by single-step weaving onto the weaving rod from a single weft that interlocks various warps according to the embodiments of the invention, as shown in FIG. 4B. The twisted ply that formed the warp were mounted on carriers so as to maintain a maximum tension of 0.2 N. The twisted ply that formed the weft was loaded on a stationary carrier that can withstand a maximum tension of 4 N. The conduits were obtained by loading electrospun polymeric yarns in the weaving apparatus. FIGS. 4C and 4D shows optical image and SEM image of woven PLLA conduits of high packing density obtained by loading the apparatus with 47 carriers, respectively. FIGS. 4E and 4F shows optical image and SEM image of woven PLLA conduits of low packing density obtained by loading the apparatus with 16 carriers, respectively. The figures illustrate the effect of carriers on the conduit packing density when the setup and conditions are otherwise identical.

Figure 5A:
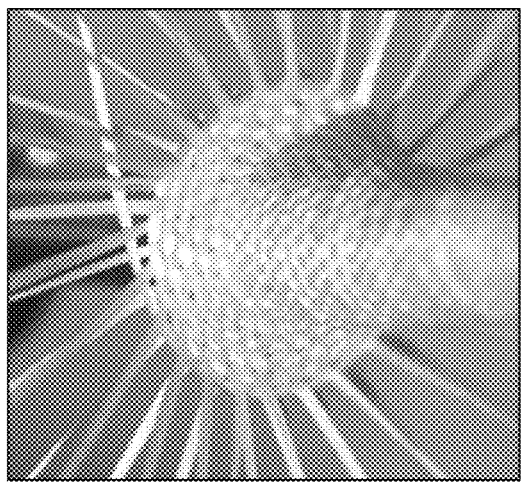
FIG. 5A shows an optical image of 0.5 mm woven conduit inside a capillary tube.
Figure 5B:
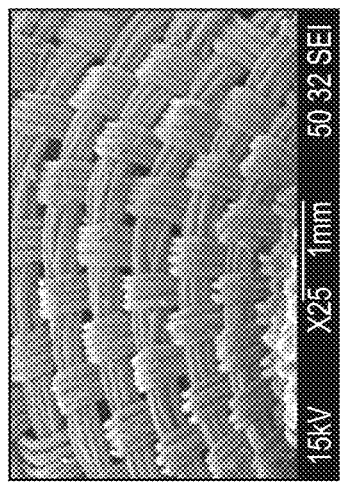
FIG. 5B shows an optical image of flexible woven conduit of diameter 4 mm.
Figure 5C:
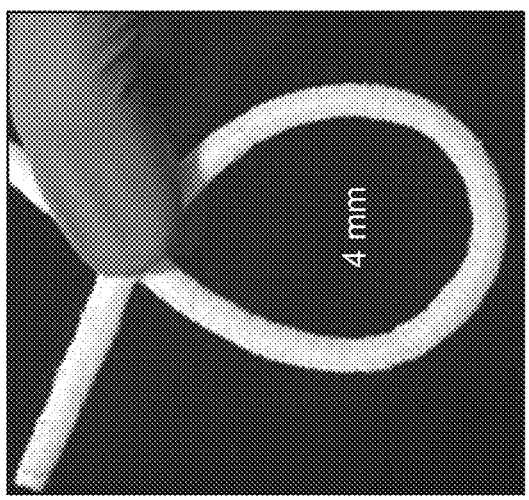
FIG. 5C depicts architecture of conduit where a minimum tension was not maintained.
Figure 5D:
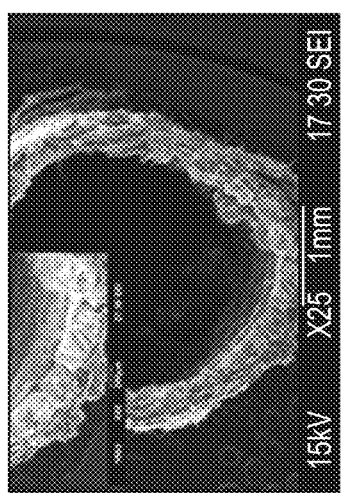
FIG. 5D shows SEM image of cross-section view of a 0.5 mm woven conduit.
Figure 5E:
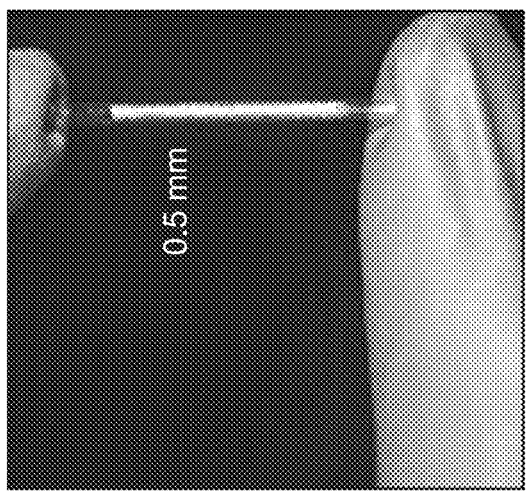
FIG. 5E shows SEM image of cross-section view of a 4 mm woven conduit.
Figure 5F:
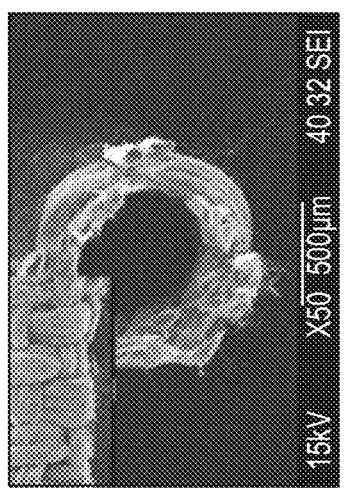
FIG. 5F shows SEM image of cross-section view of a woven conduit where minimal tension was not maintained.

A variety of small diameter conduits were fabricated. A 0.5 mm diameter woven conduit placed inside the capillary tube is shown in FIG. 5A. A 4 mm diameter fabricated woven conduit is shown in FIG. 5B. SEM micrographs of cross-sectional and lateral views for each of the 0.5 mm and 4 mm conduits are shown in FIGS. 5D and 5E, respectively. The tension of both warp and weft were adjusted in each carrier based on the strength of the yarns. Here, the warp and weft could withstand a breaking force of 1.42±0.22 N and 10.23±0.64N respectively. Packing density of the conduit measured as number of interlocks (warp and weft) of yarns per unit area was calculated from SEM micrographs. The packing density was in the range of 50 to 1000 interweaves per unit area ($cm^2$) was obtained by varying the number of carriers between 7 to 300 and/or by changing the diameter of warp/weft yarns used in the weaving process as described below. A minimal tension was always maintained on both circumferential and longitudinal yarns for proper interlocking, which otherwise leads to an open web-like structure. FIGS. 5C and 5F shows the optical and SEM micrograph for architectures formed due to inadequate tension on yarns during weaving.

FIG. 6 shows a hierarchical multiscale woven conduit fabricated from electrospun PCL-collagen (75:25) fibers (FIG. 6A-6D), and electrospun PLLA fibers (FIG. 6E-6H). The yarns were obtained by electrospinning polymeric solutions of PLLA and PCL-collagen (75:25 wt. %) using a modified collector as described in US patent, US20160168754A1. The individual fibers of PCL-collagen nanoyarns were of 183±14 nm in diameter. The individual fibers of PLLA nanoyarns were of 780±236 nm in diameter.

Figure 7A:
FIG. 7A and 7B illustrates a SEM image of cross-sectional of woven conduit made from plied circumferential yarns and plied longitudinal yarns.
Figure 7B:
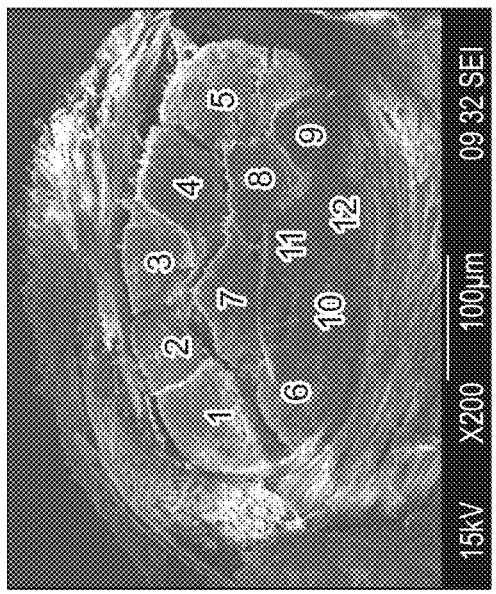

The yarns used in the conduits were bundled by plying 12 individual nanoyarns to make longitudinal yarns and 4 individual nanoyarns to make the circumferential yarn. The cross-section view of the fibers is shown in FIGS. 7A and 7B. Each yarn consisted of several hundred thousand individual nanofibers twisted into a single thread, called a nanoyarn, of ~70-200 microns diameter. The nanoyarns possess the property of hierarchy, the nanofibers comprising the yarn, and the yarns comprising the nanotextile, with progressive increase in scale. While the nanoscale can provide for enhanced biological interactions, the higher scales can impart improved mechanical strength and component integrity.

Figure 7E:
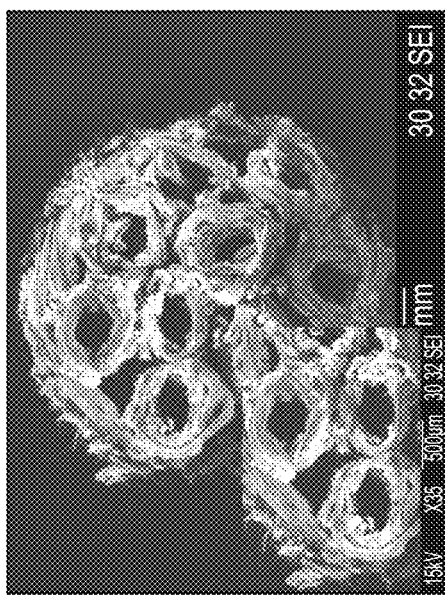
FIG. 7E shows SEM image of woven conduit with multi-channel structure.
Figure 7D:
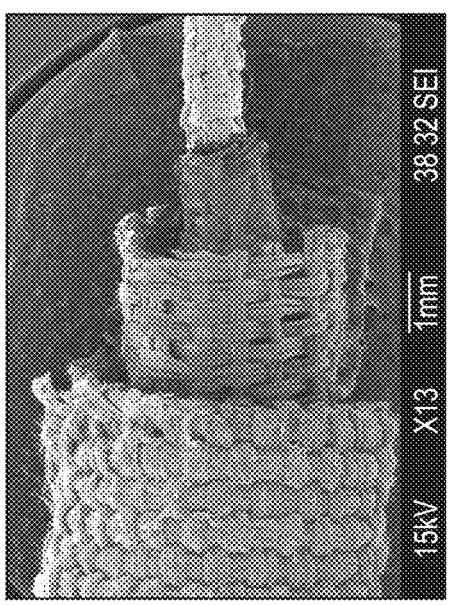
FIG. 7D shows SEM image of woven conduit with concentric structure.
Figure 7C:
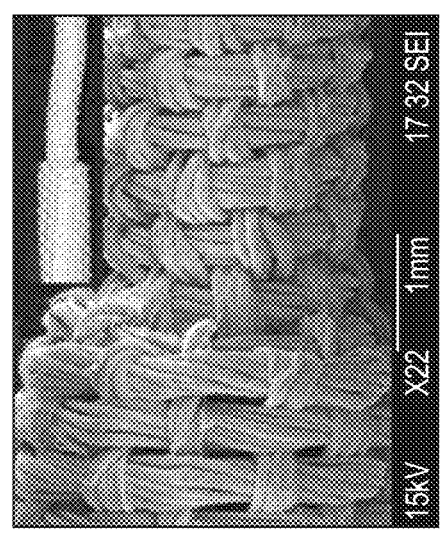
FIG. 7C shows SEM image of woven conduit with step changes in diameter.

FIG. 7C illustrates SEM image of a woven conduit fabricated with a step change in diameter which is dependent on the weaving rod diameter. The inset shows the optical image. FIGS. 7D and 7E shows hierarchical concentric and multi-channelized structures, respectively with the markings indicating individual conduits of same or different diameter. These complex multiscale conduits were fabricated by using weaving rods of different dimensions.

Figure 8A:
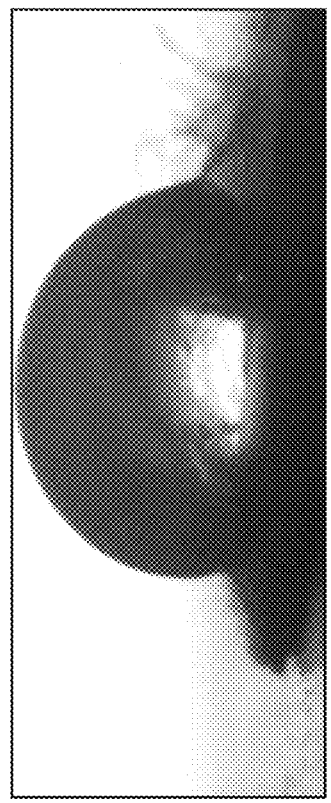
FIG. 8A shows the low wettability of a PLLA film.
Figure 8B:
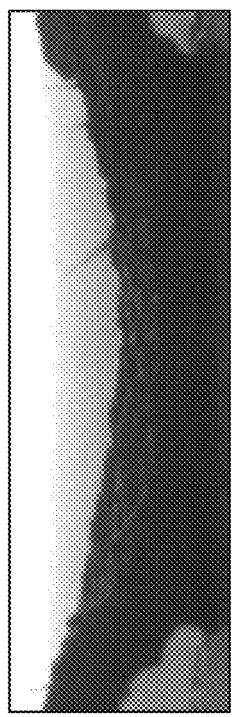
FIG. 8B shows the super hydrophilic nature of PLLA woven nanotextile.
Figure 9A:
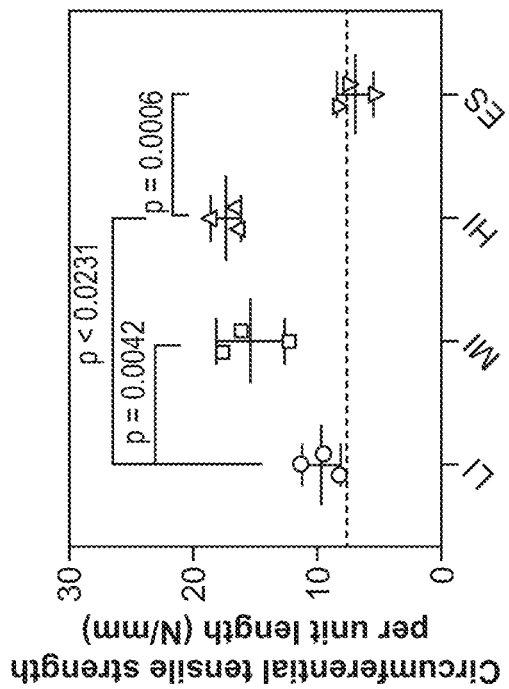
FIGS. 9A, 9B, 9C and 9D shows the circumferential tensile strength, longitudinal tensile strength, radial stiffness and suture retention strength of nanotextiles with three different material packing (LI, MI, HI) in comparison to the electrospun conduit (control) and ePTFE (commercial standard) denoted as dotted red line.
Figure 9B:
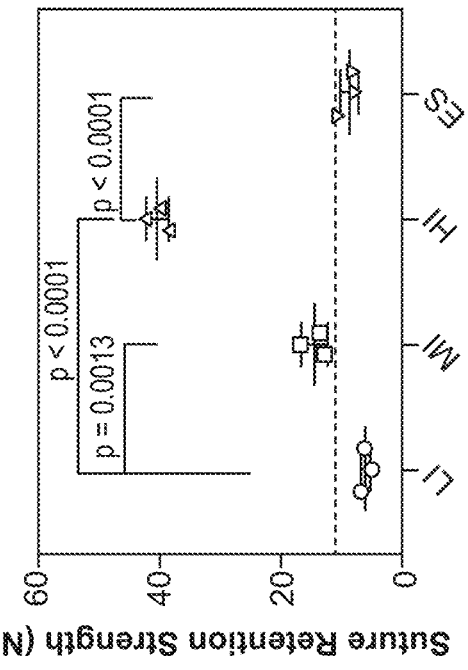
Figure 9C:
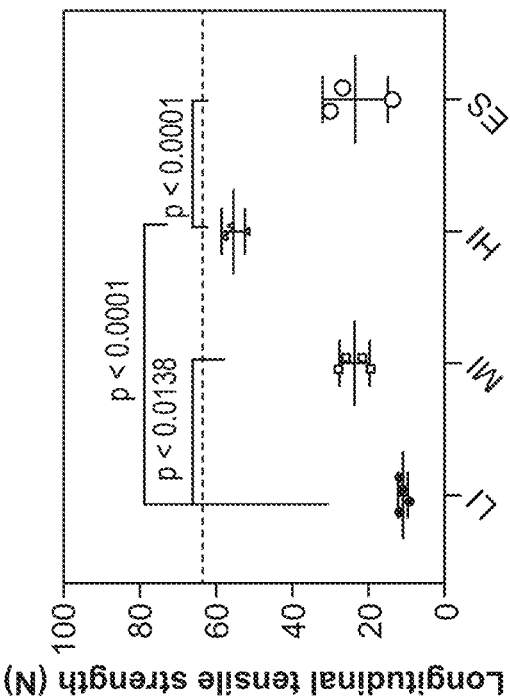
Figure 9D:
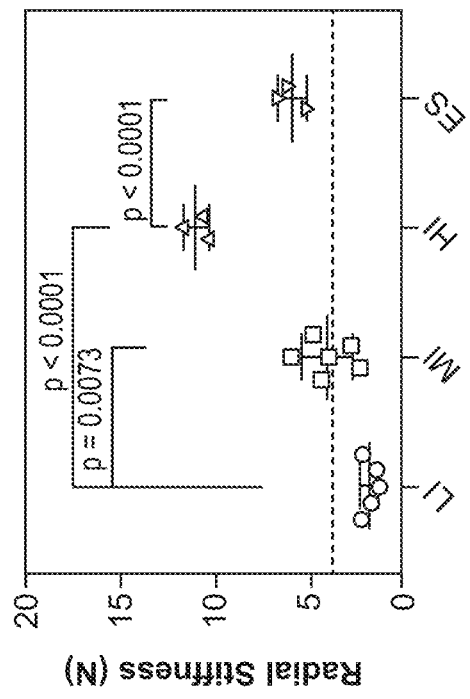
Figure 9E:
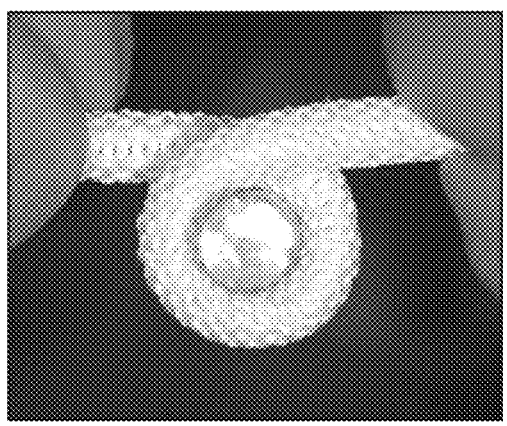
FIG. 9E shows the kink-proof nature of the nanotextile conduit which is looped around 1.5 mm rod.
Figure 9F:
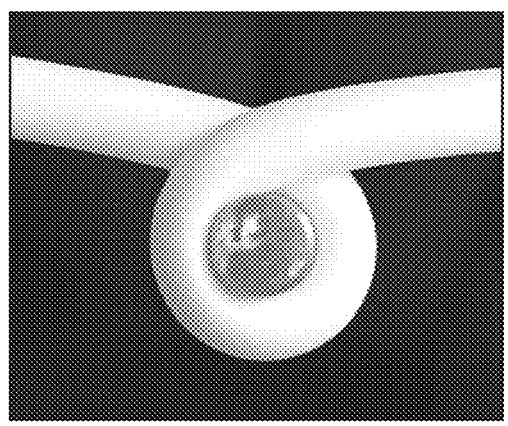
FIG. 9F shows the comparable kink-proof nature of the commercial ePTFE.

Water contact angle measurements revealed remarkable changes in the hydrophobic nature of PLLA (FIG. 8A) when woven as tightly packed aligned nanotextiles. Water drops spread almost instantaneously on the nanotextile having aligned PLLA yarns, with apparent contact angle close to zero (FIG. 8B), thus converting a hydrophobic polymer to a hydrophilic material. Another feature vital for vascular applications of nanotextiles is its mechanical characteristics. For tightly packed tubes (HI; 330 interweaves/$cm^2$), the suture retention strength, circumferential strength, tensile strength and radial stiffness were all significantly higher than for non-woven tubes (ES) and were comparable to the commercial standard (FIG. 9A-9D). Similar testing was done for moderately packed tubes (MI; 100 interweaves/$cm^2$) and loosely packed tubes (LI; 63 interweaves/$cm^2$). The woven grafts had a much smaller tendency to kink, with an average kink radius of 6 mm, compared to ePTFE (FIGS. 9E & 9F). This property implies the capability of the woven graft to bend without kinking, thereby facilitating normal blood flow and eventually patency.

Figure 10:
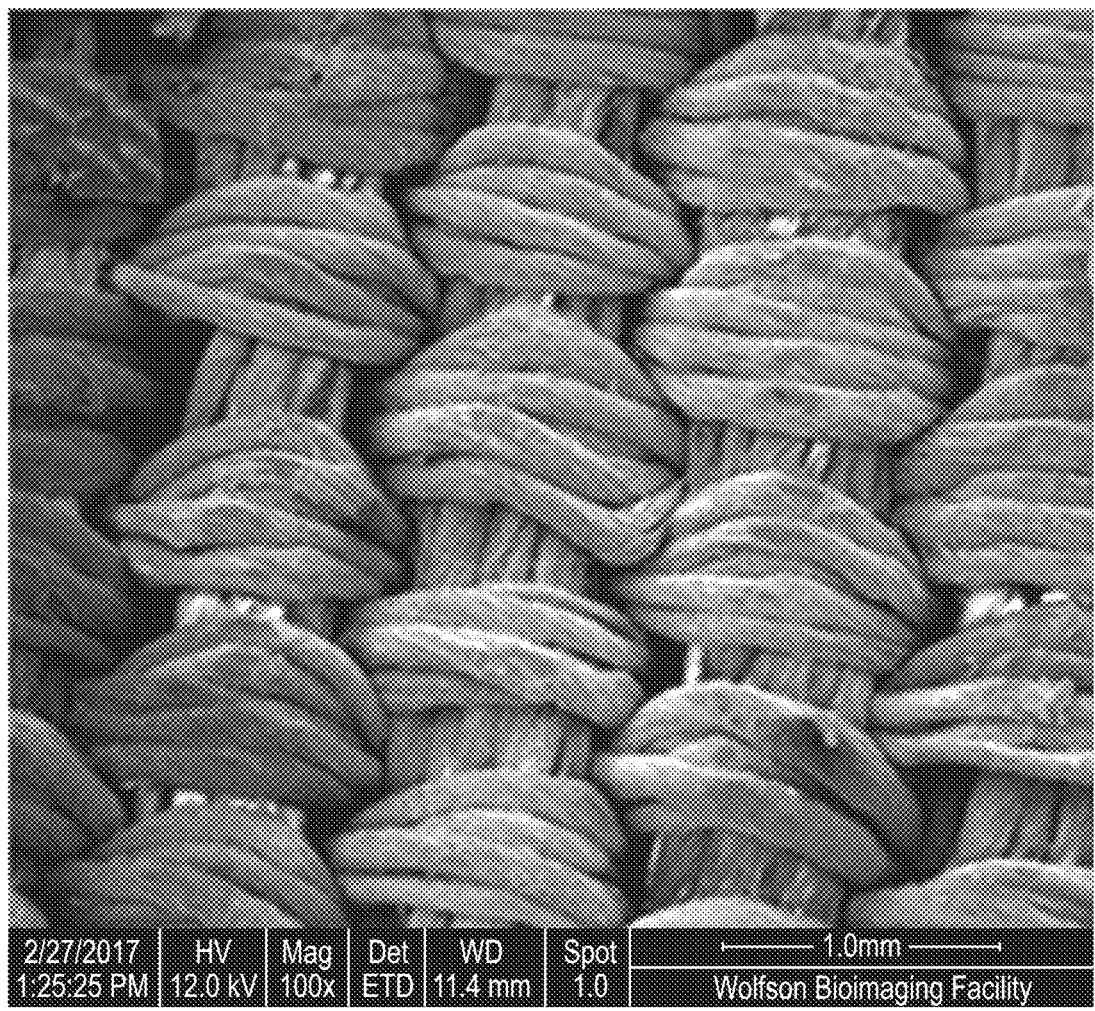
FIG. 10 shows SEM image of highly packed woven conduit used for vascular graft application.
Figure 11B:
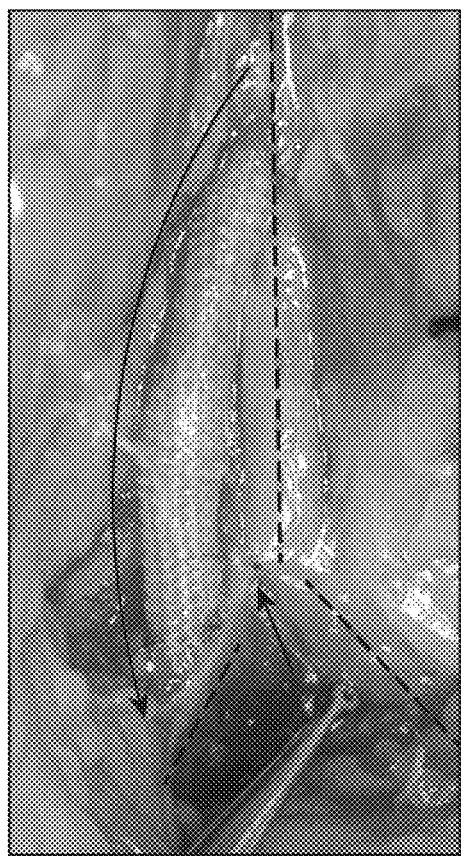
FIG. 11B shows implantation of the woven graft as aortoiliac bypass graft, with dotted line showing path of native blood flow and solid line showing blood flow via bypass route.
Figure 11D:
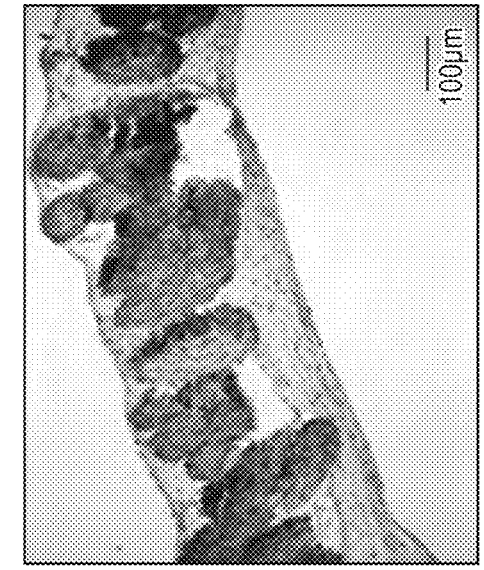
FIG. 11D illustrates H&E staining of a cross-section of the implanted area showing no signs of thrombus formation, inflammation and intimal thickening.
Figure 11A:
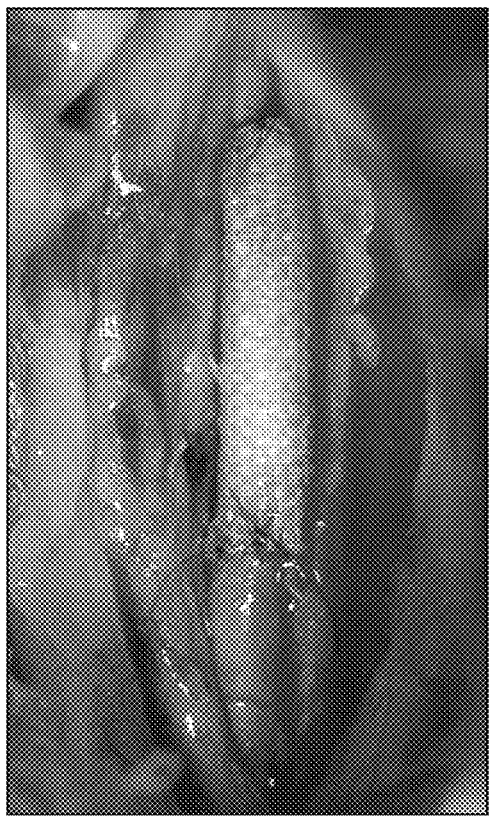
FIG. 11A shows implantation of the woven graft in rabbit abdominal aorta as interposition graft.
Figure 11C:
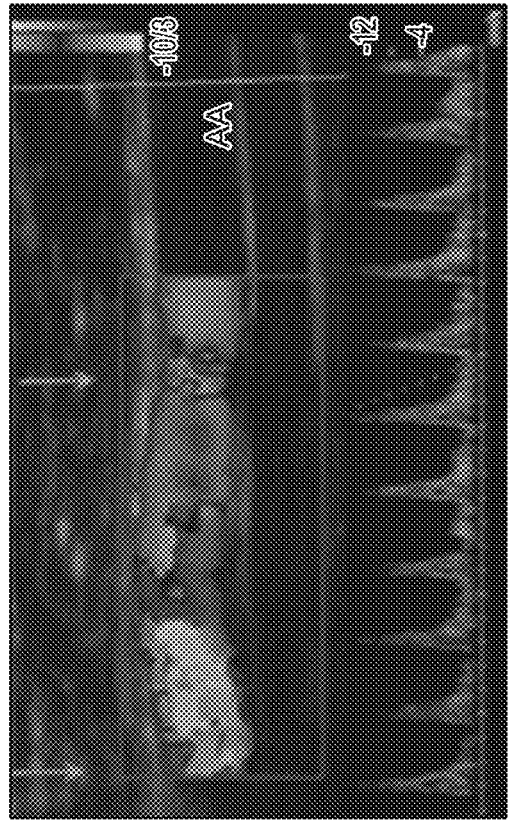
FIG. 11C depicts ultrasound image of the implanted graft showing good graft patency.

Example 2: Short-Term In Vivo Implantation of Woven Nanotextiles Based Vascular Graft in Rabbit Model Small diameter conduits fabricated using the weaving apparatus as described in Example 1, with average material packing of 690 interweaves per unit area ($cm^2$), as shown in FIG. 10, and were used for the in vivo implantation. Rabbits were anesthetized and a 4 cm incision was made on the abdomen. Abdominal aorta was exposed just above the iliac bifurcation. The woven nanotextile conduits were implanted both as interposition (FIG. 11A) as well as bypass grafts (FIG. 11B) via end-to-end and side-to-side anastomosis respectively, using polypropylene 8-0 sutures. The abdominal incision was closed using 3-0 Vicryl sutures. The animal was allowed to recover. A preliminary safety and feasibility analysis revealed the graft to be free from thrombus and aneurysm, with a pulsatile blood flow, confirmed by ultrasound (FIG. 11C). The graft could withstand the high arterial pressure without transmural or suture line bleeding. Histological evaluation of the implanted material showed no signs of acute inflammatory response in the initial 48 hours of implantation (FIG. 11D).

Figure 12A:
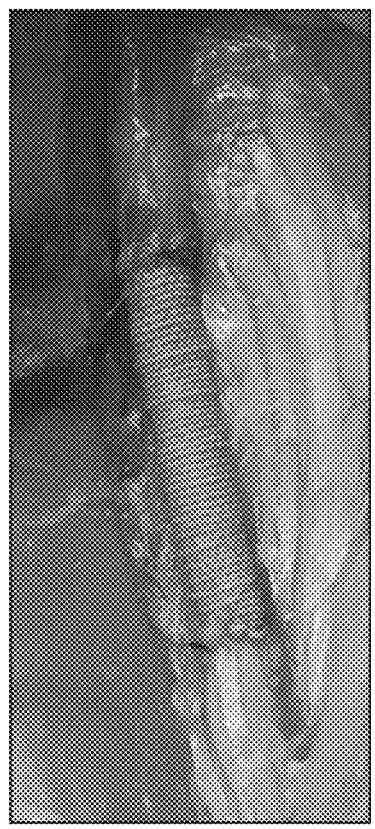
FIG. 12A shows the optical image of the implanted nanotextile based vascular graft in porcine carotid model.
Figure 12B:
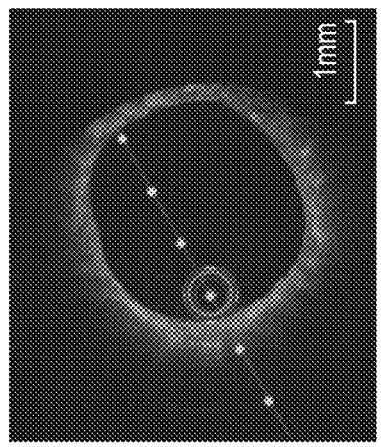
FIG. 12B shows the ex vivo optical coherence tomography of the nanotextile based vascular graft after 1 month of implantation.
Figure 12C:
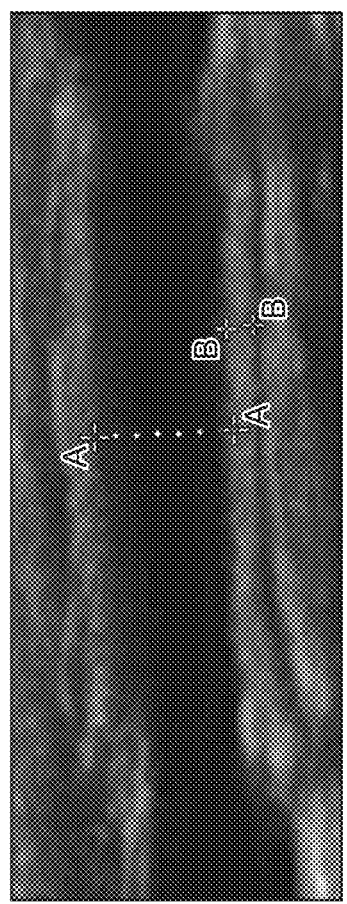
FIG. 12C shows the 2D Doppler image of longitudinal section showing the wall of nanotextile graft
Figure 12D:
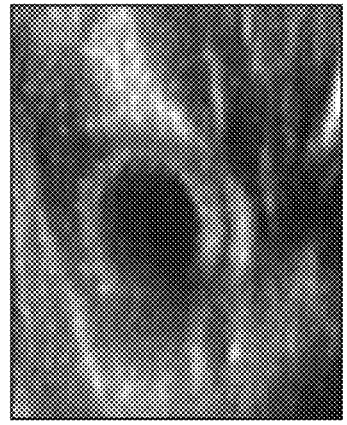
FIG. 12D shows the 2D Doppler image of cross section showing the wall of nanotextile graft.
Figure 12E:
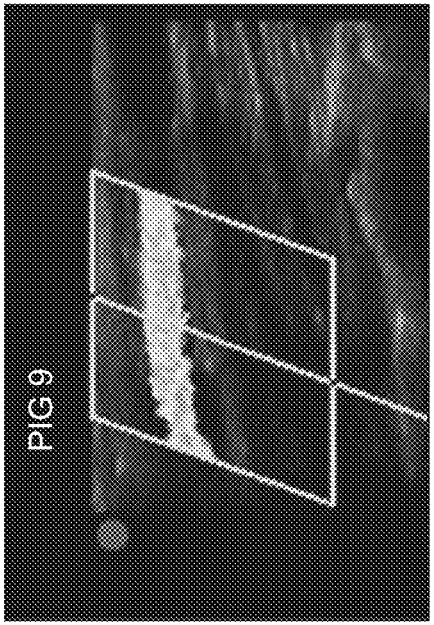
FIG. 12E shows the color Doppler of the implanted nanotextile after 1 month of implantation.
Figure 12F:
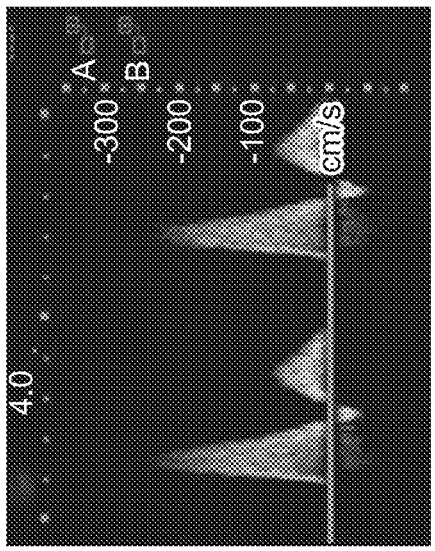
FIG. 12F shows the pulsatile blood flow through the implanted nanotextile based graft after 1 month of implantation.
Figure 12G:
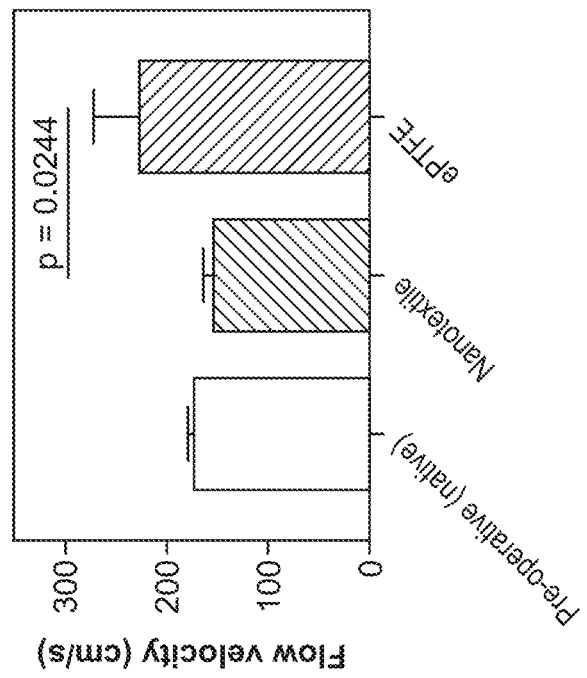
FIG. 12G shows the measure of blood flow velocity through the native vessel, nanotextile based vascular graft and commercial ePTFE.

Example 3: Long-Term In Vivo Implantation of Woven Nanotextiles Based Vascular Graft in Porcine Model Yorkshire pigs (60-80 kg) were pre-medicated with aspirin (300 mg/kg/day) for 3 days. Nanotextile tubular conduits of ~4 mm diameter, having a wall thickness of ~500 μm were implanted as interposition grafts in carotid artery via end-to-end anastomosis using polypropylene 7-0 sutures (FIG. 12A). The incision was closed using 3-0 Vicryl sutures. The nanotextile conduit was evaluated for a time duration of two and four weeks. Immediate patency of the nanotextile based vascular graft was evaluated using OCT (FIG. 12B). The inner diameter and intimal thickening of the proximal & distal anastomosis as well as mid graft portion of the graft were determined by 2D Doppler duplex sonography (FIG. 12C-12F). Ultrasound Doppler study revealed a slight increase in the blood flow velocity in ePTFE grafts with respect to the native carotid arteries, which is not statistically significant. However, the increase in flow velocity for ePTFE, which can be attributed to intimal thickening, was significant compared to the nanotextile graft (FIG. 12G). There was no post-operative change in the outer diameter of both the grafts in comparison to the values prior to implantation. This implied that there were no signs of aneurysm or any probability for graft rupture.

Figure 13A:
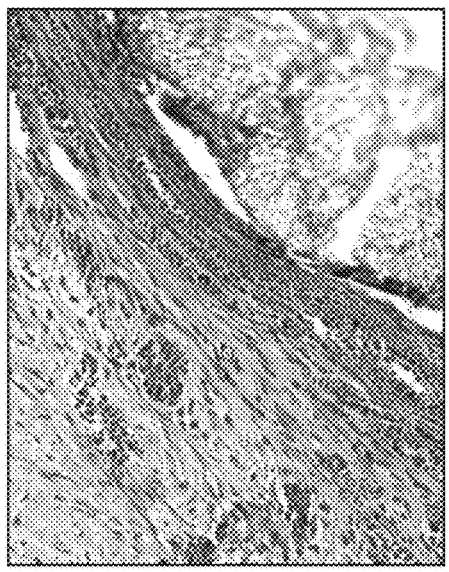
FIG. 13A depicts the H&E image (1.5× magnification) of the patent nanotextile after 2 weeks of implantation, showing no sign of occlusion
Figure 13B:
FIG. 13B depicts the H&E image (40×) of the nanotextile after 2 weeks of implantation, showing the coverage of smooth endothelial lining on the luminal surface.
Figure 13C:
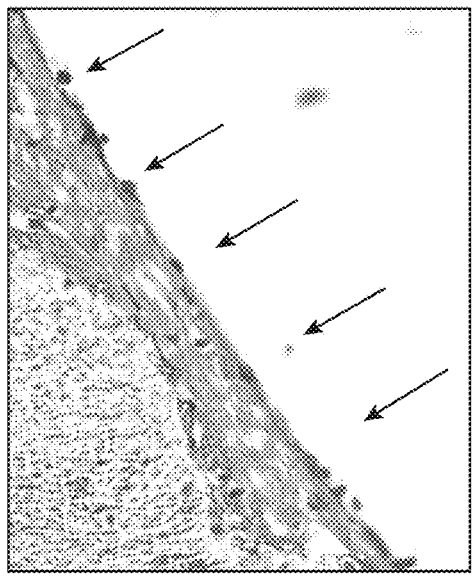
FIG. 13C depicts the H&E image (40×) of the nanotextile after 2 weeks of implantation, showing no signs of inflammatory response
Figure 13D:
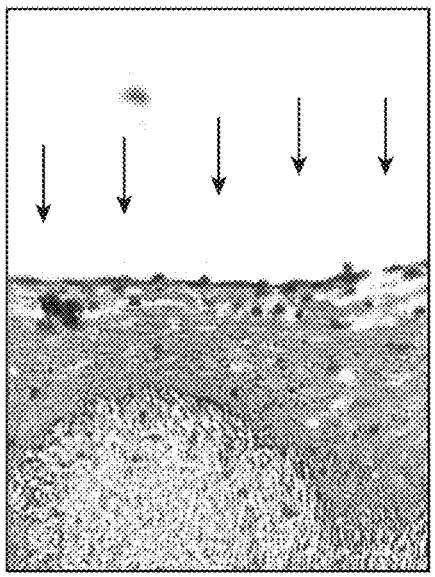
FIG. 13D depicts the H&E image (1.5× magnification) of the patent nanotextile after 4 weeks of implantation, showing no sign of occlusion and minimal intimal thickening.
Figure 13E:
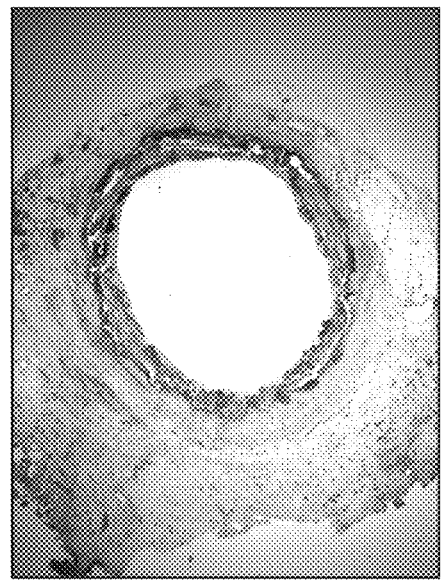
FIG. 13E depicts the H&E image (40×) of the nanotextile after 4 weeks of implantation, showing the coverage of smooth endothelial lining on the luminal surface.
Figure 13F:
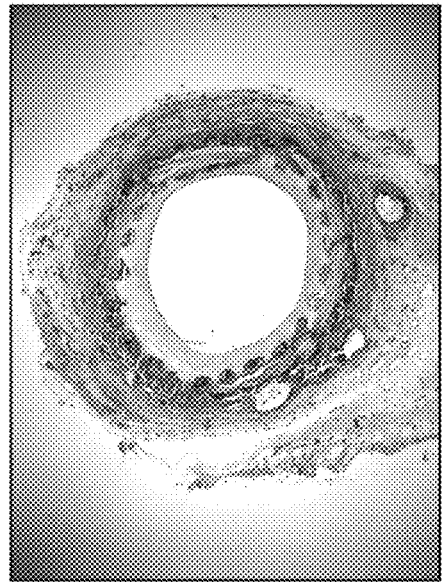
FIG. 13F depicts the H&E image (40×) of the nanotextile after 4 weeks of implantation, showing numerous neocapillary formation (depicted in circle) at the abluminal graft region.
Figure 14:
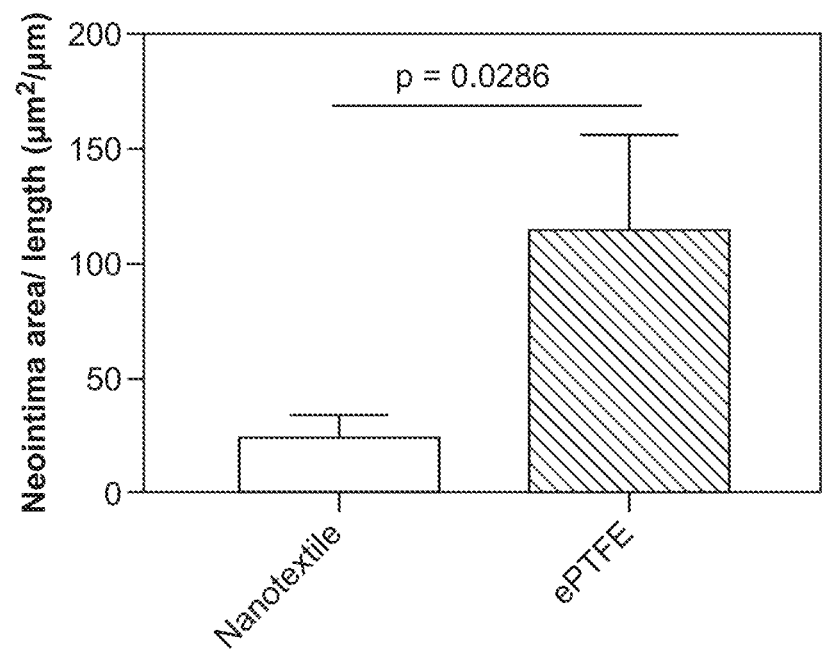
FIG. 14 shows the minimal neoimtimal thickening of the implanted nanotextile based vascular graft in comparison with the commercial standard.

Detailed histomorphometric assessments were conducted on both the synthetic grafts. Histological evaluation showed no signs of thrombi or micro thrombi on the luminal surface of nanotextile graft (FIG. 13A-13F) in contrast to ePTFE, which got occluded because of severe thrombus formation (in 1 out of 3 animals). The formation of micro thrombi has previously been reported for ePTFE grafts in carotid models. Histological evaluation of these materials showed a minimal neointimal thickening and early endothelialization within 14 days of implantation (FIG. 13B). Intimal thickening for the nanotextile graft (22.39±11.19) was significantly less than that of the control ePTFE group (114.71±41.20) (FIG. 14). In the case of woven nanotextile, intimal thickening predominantly occurred in void spaces between longitudinal and circumferential yarns, resulting in a uniform flow surface. This did not affect the graft patency, nor significantly reduce the luminal area in comparison to ePTFE. The nanotextile based graft implanted for 4 weeks showed higher number of neocapillary formation, which is a desirable feature for graft healing.

What is claimed is:

1. A weaving apparatus for making woven nanotextile conduit, comprising:
    a drum assembly mounted on a supporting platform, the drum assembly comprising:
        a first set of shuttling rods attached equidistant along the circumference of first disc;
        a second set of shutting rods attached equidistant along the circumference of a second disc, wherein the first set and second set of shuttling rods are aligned to form a closed drum assembly;
        a stationary carrier comprising a bobbin loaded with nano- or micro-fiber based polymeric weft yarn;
        a plurality of movable carriers loaded in each of the first set of shuttling rods, wherein each of the movable carriers comprise bobbins loaded with nano- or micro-fiber based polymeric warp yarns, wherein the movable carriers are configured to shuttle between the first set of rods and the second set of rods on alignment thereby interlocking the nano- or micro-fiber based warp and weft yarn; and
        a weaving rod of predetermined diameter mounted on the first disc, wherein the rod is configured to secure the warp yarns and the base weft yarns from the carriers at predetermined tension; and
    the supporting platform comprising: a geared motor system configured for synchronous rotation of the first and second discs after shuttling of each movable carrier.

* * * * *